US008815807B2

(12) United States Patent
Nagai et al.

(10) Patent No.: US 8,815,807 B2
(45) Date of Patent: Aug. 26, 2014

(54) PEPTIDES AND PEPTIDE COMPOSITIONS HAVING OSTEOINDUCTIVE ACTIVITY

(75) Inventors: Shigemi Nagai, Lexington, MA (US); Masazumi Nagai, Lexington, MA (US); Mindy Sungmin Gil, Boston, MA (US)

(73) Assignee: President and Fellows of Harvard College, Cambridge, MA (US)

(*) Notice: Subject to any disclaimer, the term of this patent is extended or adjusted under 35 U.S.C. 154(b) by 159 days.

(21) Appl. No.: 13/309,734

(22) Filed: Dec. 2, 2011

(65) Prior Publication Data

US 2012/0148681 A1 Jun. 14, 2012

Related U.S. Application Data

(63) Continuation of application No. PCT/US2010/037207, filed on Jun. 3, 2010, which is a continuation-in-part of application No. 12/477,186, filed on Jun. 3, 2009, now abandoned.

(60) Provisional application No. 61/183,716, filed on Jun. 3, 2009, provisional application No. 61/130,777, filed on Jun. 3, 2008.

(51) Int. Cl.

| | |
|---|---|
| ***A61K 38/08*** | (2006.01) |
| ***A61K 38/10*** | (2006.01) |
| ***C07K 7/06*** | (2006.01) |
| ***C07K 7/08*** | (2006.01) |
| ***C07K 17/02*** | (2006.01) |
| ***C40B 60/12*** | (2006.01) |

(52) U.S. Cl.
CPC .................................... *C40B 60/12* (2013.01)
USPC ......... 514/16.7; 514/21.5; 514/21.6; 530/327

(58) Field of Classification Search
None
See application file for complete search history.

(56) References Cited

U.S. PATENT DOCUMENTS

| | | | | |
|---|---|---|---|---|
| 5,096,815 | A | 3/1992 | Ladner et al. | |
| 5,198,346 | A | 3/1993 | Ladner et al. | |
| 5,223,409 | A | 6/1993 | Ladner et al. | |
| 5,403,484 | A | 4/1995 | Ladner et al. | |
| 5,521,319 | A | 5/1996 | Huber et al. | |
| 5,563,220 | A | 10/1996 | Webber et al. | |
| 5,571,698 | A | 11/1996 | Ladner et al. | |
| 6,150,123 | A | 11/2000 | Cosma | |
| 6,436,681 | B1 | 8/2002 | Schroder et al. | |
| 7,589,170 | B1 | 9/2009 | Smythe et al. | |
| 7,691,968 | B2 | 4/2010 | Evans et al. | |
| 2004/0214272 | A1* | 10/2004 | La Rosa et al. | 435/69.1 |
| 2007/0271630 | A1 | 11/2007 | Boukharov et al. | |

OTHER PUBLICATIONS

Barrilleaux et al. "Review: Ex Vivo Engineering of Living Tissues with Adult Stem Cells" Tiss Eng, 2006, vol. 12, pp. 3007-3019.
Katti et al. "Crystal structure of Thioredoxin from *Escherichia coli* at 1-68 A Resolution" J Mol Biol, 1990, vol. 212, pp. 167-184.
Lu et al. "Expression of thioredoxin random peptide libraries on the *Escherichia coli* cell surface as functional fusions to flagellin: a system designed for exploring protein-protein interactions." Bio/Technol, 1995, vol. 13, pp. 366-372.
Mieschendahl et al. "A Novel Prophage. Independent trp Regulated Lambda PL Expression System" Bio/Technol,1986, vol. 4, pp. 802-808.
Quintana et al. "Morphogenetic and Regulatory Mechanisms During Developmental Chondrogenesis: New Paradigms for Cartilage Tissue Engineering" Tiss Eng: Part B, 2009, vol. 15, pp. 29-41.

* cited by examiner

*Primary Examiner* — Karlheinz R Skowronek
*Assistant Examiner* — Lianko Garyu
(74) *Attorney, Agent, or Firm* — Lawson & Weitzen LLP; Sonia K. Guterman; Anna E. Stanford

(57) ABSTRACT

Compositions and kits are provided having a peptide having an amino acid sequence that binds to eukaryotic cells and effects differentiation and support growth of the cells. Peptide-scaffold compositions containing at least one peptide or combinations of peptides are therapeutic agents for stimulating and promoting osteogenic activity and osteoinduction activity for cells. The scaffold is for example apatite, natural cancellous bone, demineralized natural cancellous bone, collagen, calcium phosphate, or hydroxyapatite.

14 Claims, 6 Drawing Sheets

Fig. 1
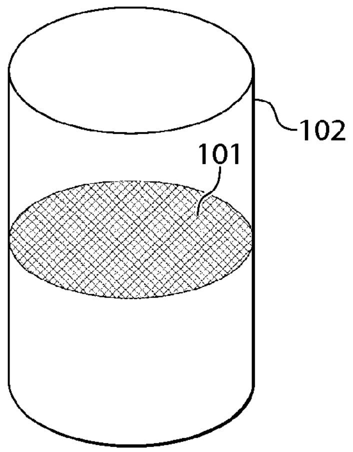
Fig. 1A
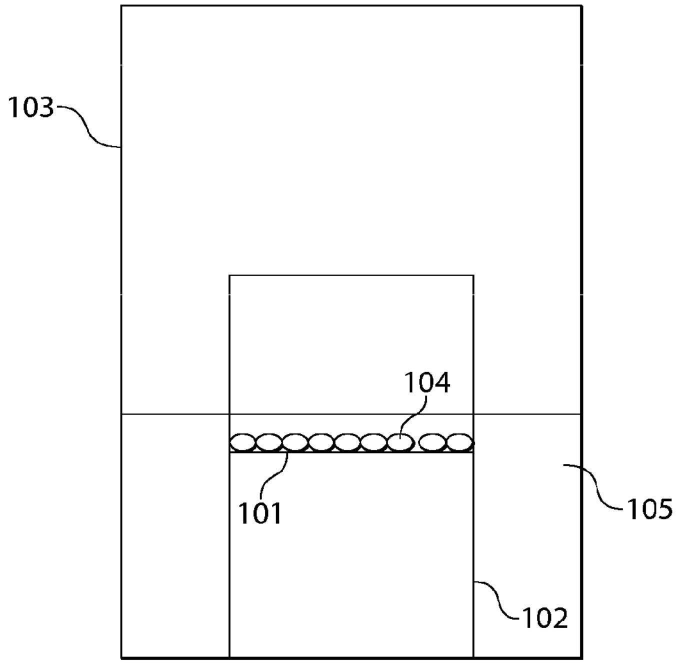
Fig. 1B

Fig. 1
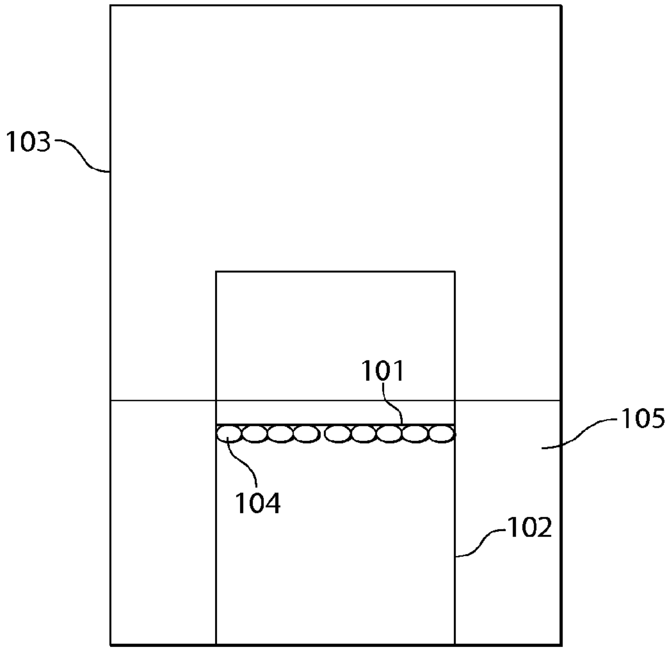
Fig. 1C
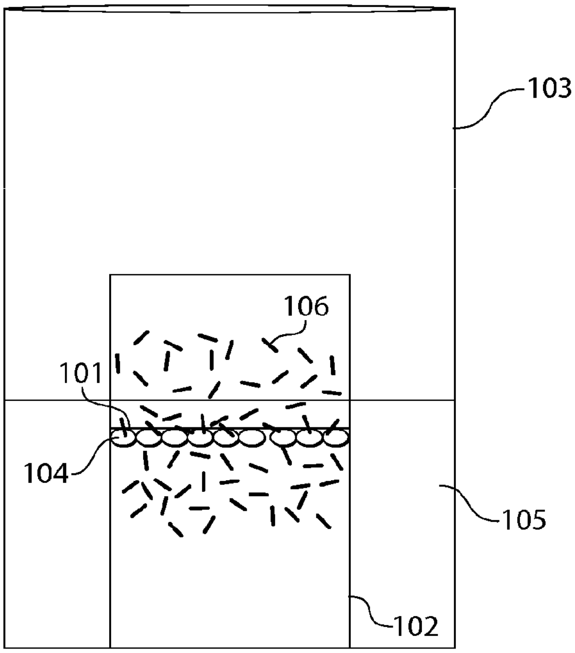
Fig. 1D

Fig. 2
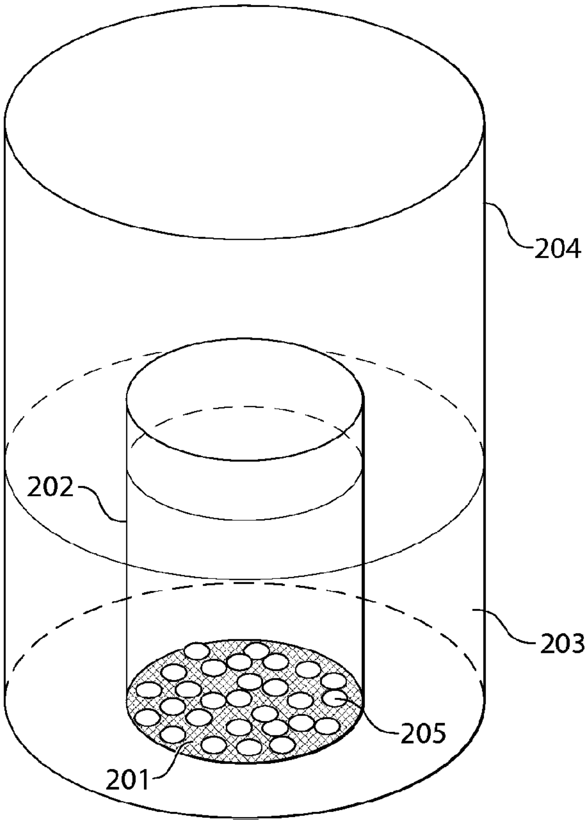
Fig. 2A
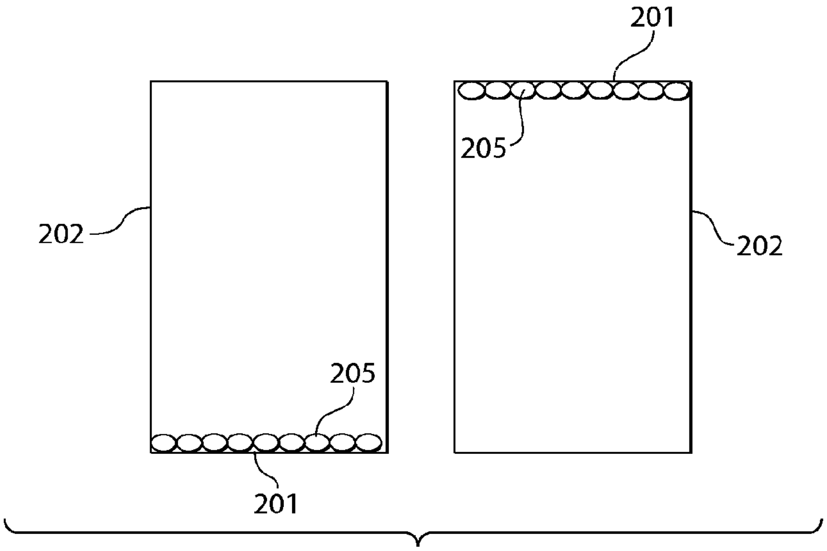
Fig. 2B

Fig. 2
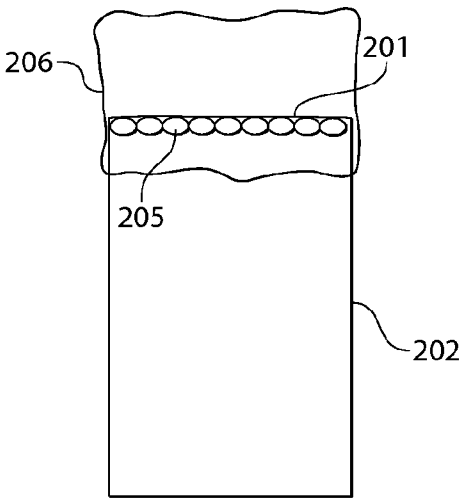
Fig. 2C
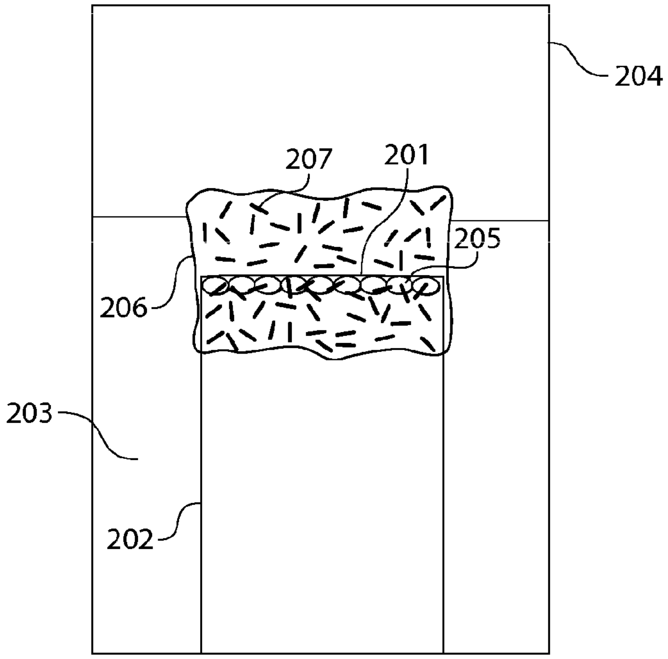
Fig. 2D

SEQUENCE LISTING

```
<160> NUMBER OF SEQ ID NOS: 27

<210> SEQ ID NO 1
<211> LENGTH: 8
<212> TYPE: PRT
<213> ORGANISM: Artificial Sequence
<220> FEATURE:
<223> OTHER INFORMATION: The protein was designed and synthesized
<220> FEATURE:
<221> NAME/KEY: misc_feature
<222> LOCATION: (4)..(5)
<223> OTHER INFORMATION: Xaa can be any naturally occurring amino acid

<400> SEQUENCE: 1

Arg Gly Asn Xaa Xaa Gly Gly Arg
1               5


<210> SEQ ID NO 2
<211> LENGTH: 12
<212> TYPE: PRT
<213> ORGANISM: Artificial Sequence
<220> FEATURE:
<223> OTHER INFORMATION: The protein was designed and synthesized

<400> SEQUENCE: 2

Val Phe Leu Arg Gly Asn Asn Ser Gly Gly Arg Ser
1               5                   10


<210> SEQ ID NO 3
<211> LENGTH: 12
<212> TYPE: PRT
<213> ORGANISM: Artificial Sequence
<220> FEATURE:
<223> OTHER INFORMATION: The protein was designed and synthesized

<400> SEQUENCE: 3

Gly Lys Ile His Arg His Arg Gly Gln Ala Val Glu
1               5                   10


<210> SEQ ID NO 4
<211> LENGTH: 12
<212> TYPE: PRT
<213> ORGANISM: Artificial Sequence
<220> FEATURE:
<223> OTHER INFORMATION: The protein was designed and synthesized

<400> SEQUENCE: 4

His Ile Arg Gln Met Pro Val Arg Ala Gly Leu Ser
1               5                   10


<210> SEQ ID NO 5
<211> LENGTH: 12
<212> TYPE: PRT
<213> ORGANISM: Artificial Sequence
```

<220> FEATURE:
<223> OTHER INFORMATION: The protein was designed and synthesized
<220> FEATURE:
<221> NAME/KEY: misc_feature
<222> LOCATION: (9)..(9)
<223> OTHER INFORMATION: Xaa can be any naturally occurring amino acid

<400> SEQUENCE: 5

Arg Gln Gly Val Gly Ser Asn Gly Xaa Ile Gln Lys
1 5 10

<210> SEQ ID NO 6
<211> LENGTH: 12
<212> TYPE: PRT
<213> ORGANISM: Artificial Sequence
<220> FEATURE:
<223> OTHER INFORMATION: The protein was designed and synthesized

<400> SEQUENCE: 6

Glu Ser His Cys Leu Leu Gly Ile Ser Cys Val Leu
1 5 10

<210> SEQ ID NO 7
<211> LENGTH: 11
<212> TYPE: PRT
<213> ORGANISM: Artificial Sequence
<220> FEATURE:
<223> OTHER INFORMATION: The protein was designed and synthesized

<400> SEQUENCE: 7

Gln Gln Leu Gln Gln Asn Val Ile Leu Glu Thr
1 5 10

<210> SEQ ID NO 8
<211> LENGTH: 11
<212> TYPE: PRT
<213> ORGANISM: Artificial Sequence
<220> FEATURE:
<223> OTHER INFORMATION: The protein was designed and synthesized

<400> SEQUENCE: 8

Arg Ser Lys Leu Val Glu Phe Arg Thr Thr Gly
1 5 10

<210> SEQ ID NO 9
<211> LENGTH: 11
<212> TYPE: PRT
<213> ORGANISM: Artificial Sequence
<220> FEATURE:
<223> OTHER INFORMATION: The protein was designed and synthesized

<400> SEQUENCE: 9

Arg Asn Trp Arg Met Ser Arg Arg Gly Gly Met
1 5 10

<210> SEQ ID NO 10
<211> LENGTH: 12
<212> TYPE: PRT
<213> ORGANISM: Artificial Sequence
<220> FEATURE:
<223> OTHER INFORMATION: The protein was designed and synthesized

<400> SEQUENCE: 10

Cys Val Arg Gly Arg Gly Arg Met Ala Gly Ser Val
1 5 10

<210> SEQ ID NO 11

<211> LENGTH: 12
<212> TYPE: PRT
<213> ORGANISM: Artificial Sequence
<220> FEATURE:
<223> OTHER INFORMATION: The protein was designed and synthesized

<400> SEQUENCE: 11

Ile Thr Arg Gly Glu Leu Ala Thr Val Arg Arg Ser
1 5 10

<210> SEQ ID NO 12
<211> LENGTH: 11
<212> TYPE: PRT
<213> ORGANISM: Artificial Sequence
<220> FEATURE:
<223> OTHER INFORMATION: The protein was designed and synthesized

<400> SEQUENCE: 12

Leu Arg Leu Gly Val Gly Met Gly Arg Thr Cys
1 5 10

<210> SEQ ID NO 13
<211> LENGTH: 11
<212> TYPE: PRT
<213> ORGANISM: Artificial Sequence
<220> FEATURE:
<223> OTHER INFORMATION: The protein was designed and synthesized

<400> SEQUENCE: 13

Glu Arg Phe Ala Gly Asn Arg Asn Gln Leu Gln
1 5 10

<210> SEQ ID NO 14
<211> LENGTH: 11
<212> TYPE: PRT
<213> ORGANISM: Artificial Sequence
<220> FEATURE:
<223> OTHER INFORMATION: The protein was designed and synthesized

<400> SEQUENCE: 14

Gly Gly Leu Gly Ser Val Gly Trp Tyr Trp Ala
1 5 10

<210> SEQ ID NO 15
<211> LENGTH: 12
<212> TYPE: PRT
<213> ORGANISM: Artificial Sequence
<220> FEATURE:
<223> OTHER INFORMATION: The protein was designed and synthesized

<400> SEQUENCE: 15

Gly Cys Gly Lys Glu Arg Gly Arg Arg Ala Leu Lys
1 5 10

<210> SEQ ID NO 16
<211> LENGTH: 12
<212> TYPE: PRT
<213> ORGANISM: Artificial Sequence
<220> FEATURE:
<223> OTHER INFORMATION: The protein was designed and synthesized

<400> SEQUENCE: 16

Gly Gln Glu Arg Leu Trp Ala Phe Arg Trp Val Pro
1 5 10

<210> SEQ ID NO 17
<211> LENGTH: 12

<212> TYPE: PRT
<213> ORGANISM: Artificial Sequence
<220> FEATURE:
<223> OTHER INFORMATION: The protein was designed and synthesized

<400> SEQUENCE: 17

Arg Gly Val Leu Arg Val Gly Thr Gly Arg Ser Glu
1 5 10

<210> SEQ ID NO 18
<211> LENGTH: 12
<212> TYPE: PRT
<213> ORGANISM: Artificial Sequence
<220> FEATURE:
<223> OTHER INFORMATION: The protein was designed and synthesized

<400> SEQUENCE: 18

Ile Thr Arg Gly Glu Leu Ala Thr Val Arg Arg Ser
1 5 10

<210> SEQ ID NO 19
<211> LENGTH: 12
<212> TYPE: PRT
<213> ORGANISM: Artificial Sequence
<220> FEATURE:
<223> OTHER INFORMATION: The protein was designed and synthesized

<400> SEQUENCE: 19

Arg Pro Ala Leu Arg Leu Gly Leu Ile Gly Pro Ser
1 5 10

<210> SEQ ID NO 20
<211> LENGTH: 11
<212> TYPE: PRT
<213> ORGANISM: Artificial Sequence
<220> FEATURE:
<223> OTHER INFORMATION: The protein was designed and synthesized
<220> FEATURE:
<221> NAME/KEY: misc_feature
<222> LOCATION: (11)..(11)
<223> OTHER INFORMATION: Xaa can be any naturally occurring amino acid

<400> SEQUENCE: 20

Thr Arg Thr Ser Val Asp Ala Pro Ile Arg Xaa
1 5 10

<210> SEQ ID NO 21
<211> LENGTH: 12
<212> TYPE: PRT
<213> ORGANISM: Artificial Sequence
<220> FEATURE:
<223> OTHER INFORMATION: The protein was designed and synthesized

<400> SEQUENCE: 21

Ser Lys Ala Leu Arg Gly Val Gly Ser Val Ala Ser
1 5 10

<210> SEQ ID NO 22
<211> LENGTH: 11
<212> TYPE: PRT
<213> ORGANISM: Artificial Sequence
<220> FEATURE:
<223> OTHER INFORMATION: The protein was designed and synthesized

<400> SEQUENCE: 22

Arg Arg Gly Gln Asp Arg Gly His Glu Pro Lys
1 5 10

-continued

```
<210> SEQ ID NO 23
<211> LENGTH: 10
<212> TYPE: PRT
<213> ORGANISM: Artificial Sequence
<220> FEATURE:
<223> OTHER INFORMATION: The protein was designed and synthesized

<400> SEQUENCE: 23

Cys Leu Leu Gly Ile Thr Cys Ala Ile Pro
1               5                   10


<210> SEQ ID NO 24
<211> LENGTH: 15
<212> TYPE: PRT
<213> ORGANISM: Artificial Sequence
<220> FEATURE:
<223> OTHER INFORMATION: The protein was designed and synthesized

<400> SEQUENCE: 24

Gly Thr Pro Gly Pro Gln Gly Ile Ala Gly Gln Arg Gly Val Val
1               5                   10                  15


<210> SEQ ID NO 25
<211> LENGTH: 20
<212> TYPE: DNA
<213> ORGANISM: Artificial Sequence
<220> FEATURE:
<223> OTHER INFORMATION: The sequencing primer was designed and
      synthesized

<400> SEQUENCE: 25

tagcatcgtc cagcgctttc                                                   20


<210> SEQ ID NO 26
<211> LENGTH: 20
<212> TYPE: PRT
<213> ORGANISM: Artificial Sequence
<220> FEATURE:
<223> OTHER INFORMATION: The protein was designed and sythesized

<400> SEQUENCE: 26

Asn Ser Val Asn Ser Lys Ile Pro Lys Ala Cys Cys Val Pro Thr Glu
1               5                   10                  15

Leu Ser Ala Ile
            20


<210> SEQ ID NO 27
<211> LENGTH: 15
<212> TYPE: PRT
<213> ORGANISM: Artificial Sequence
<220> FEATURE:
<223> OTHER INFORMATION: The protein was designed and synthesized

<400> SEQUENCE: 27

Gly Thr Pro Gly Pro Gln Gly Ile Ala Gly Gln Arg Gly Val Val
1               5                   10                  15
```

PEPTIDES AND PEPTIDE COMPOSITIONS HAVING OSTEOINDUCTIVE ACTIVITY

RELATED APPLICATIONS

The present application claims the benefit of international application number PCT/US2010/037207 filed Jun. 3, 2010 which claims the benefit of U.S. provisional application Ser. No. 61/183,716 filed Jun. 3, 2009 in the U.S. Patent and Trademark Office, and the present application also claims the benefit of U.S. utility application Ser. No. 12/477,186 filed Jun. 3, 2009 which claims the benefit of U.S. provisional application Ser. No. 61/130,777 filed Jun. 3, 2008, which are hereby incorporated herein by reference in their entireties.

TECHNICAL FIELD

Peptides are provided that were isolated by a biopanning device and system, and the peptides function as osteogenic and osteoinductive agents. Peptide-scaffold compositions that stimulate growth and differentiation of cells and osteogenic activity, and methods and kits of isolating and using the peptides are provided.

BACKGROUND

Extracellular matrix (ECM) in biological tissue is involved in recruitment, adhesion, survival, proliferation and differentiation of cells during embryonic morphogenesis, development and repair of tissues. ECM-mimetic biomaterials play a key role in successful therapy in regenerative medicine. Information obtained from knowledge of protein components of ECM is needed for design of these biomaterials utilizes.

ECM is composed of structural proteins generally found in abundant quantities, and also contains smaller amounts of specialized proteins. Structural proteins include collagens, elastins and laminins which have been well characterized. Specialized proteins however remain largely uncharacterized. Detailed knowledge of functions of ECM proteins is needed to facilitate design of ECM mimetics.

Proteomics techniques have been largely unsuccessful in determining peptide sequences of protein features that are displayed on the surface of ECM proteins. There is a need to develop tools for characterizing functional aspects of protein components of the ECM surface, such as devices, methods, and systems to identify peptides displayed on proteins that function as ligands, and to identify corresponding modulatory proteins.

SUMMARY

An embodiment of the invention provides a peptide composition having an amino acid sequence: VFLRGNNSGGRS (SEQ ID NO:2), GKIHRHRGQAVE (SEQ ID NO: 3), HIRQMPVRAGLS (SEQ ID NO: 4), RQGVGSNGXIQK (SEQ ID NO: 5), ESHCLLGISCVL (SEQ ID NO: 6), QQLQQNVILET (SEQ ID NO: 7), RSKLVEFRTTG (SEQ ID NO: 8), RNWRMSRRGGM (SEQ ID NO: 9), CVRGRGRMAGSV (SEQ ID NO: 10), ITRGELATVRRS (SEQ ID NO: 11), LRLGVGMGRTC (SEQ ID NO: 12), ERFAGNRNQLQ (SEQ ID NO: 13), GGLGSVGWYWA (SEQ ID NO: 14), GCGKERGRRALK (SEQ ID NO: 15), GQERLWAFRWVP (SEQ ID NO: 16), RGVLRVGTGRSE (SEQ ID NO: 17), ITRGELATVRRS (SEQ ID NO: 18), RPALRLGLIGPS (SEQ ID NO: 19), TRTSVDAPIRX (SEQ ID NO: 20), SKALRGVGSVAS (SEQ ID NO: 21) RRGQDRGHEPK (SEQ ID NO: 22), CLLGITCAIP (SEQ ID NO: 23), and a portion of any of these sequences. The sequences are indicated using the one letter amino acid code.

In a related embodiment, the amino acid sequence has an affinity for an extracellular matrix (ECM) component. In various embodiments, the ECM component is an aggrecan, a collagen, and a hyaluronan.

An embodiment of the invention herein provides a peptide composition including an amino acid sequence RGNxxGGR (SEQ ID NO: 1), such that RGN and GGR are sequences indicated using the one letter amino acid code, and x indicates any amino acid, for example, R is arginine, G is glycine, and N is asparagine. In general, x is a naturally occurring amino acid. Alternatively, x is non-naturally occurring and synthetic, for example x is a D amino acid. In various embodiments, x is a peptide nucleic acid. The amino acid sequence in the composition for example includes VFLRGNNSGGRS (SEQ ID NO:2).

In related embodiments, the amino acid sequence of the peptide composition has a cell stimulatory activity for at least one of growth and differentiation. In general, the cell is a eukaryotic cell.

In various embodiments, the activity stimulates at least one of a pre-osteoblastic cell or an osteoblast cell. The stimulatory activity is greater than that of a control, which is for example, a tripeptide RGD, or a peptide with amino acid sequence GTPGPQGIAGQRGVV (SEQ ID NO: 24). This peptide with amino acid sequence (SEQ ID NO: 24) is a commercially available product PepGen P-15 (Dentsply-Friadent Inc., Tulsa, Okla.), a synthetic bio-mimetic of a 15 amino acid sequence of type I collagen. In various embodiments, the amino acid sequence in the peptide composition further has an affinity for an extracellular matrix (ECM) component that is greater than that of the P-15 peptide.

The peptide composition is at least about 11 or about 12 amino acids to about 100 amino acids in length. For example, the peptide composition is at least about 20 amino acids to about 50 amino acids in length.

In related embodiments, the amino acid sequence includes an amino acid analog, an amino acid derivative, or a conservative substitution of an amino acid residue. For example, an amino acid analog-containing peptide is resistant to protease and peptidase degradation that would occur in presence of serum, compared to a control peptide identical in sequence and lacking the amino acid analog.

An embodiment of the invention provides a bone-substitute scaffold complex that includes a bone substitute scaffold which is at least one of: natural cancellous bone, demineralized natural cancellous bone, collagen, calcium phosphate, and hydroxyapatite; and also includes at least one peptide having amino acid sequence: VFLRGNNSGGRS (SEQ ID NO:2), GKIHRHRGQAVE (SEQ ID NO: 3), HIRQMPVRAGLS (SEQ ID NO: 4), RQGVGSNGXIQK (SEQ ID NO: 5), ESHCLLGISCVL (SEQ ID NO: 6), QQLQQNVILET (SEQ ID NO: 7), RSKLVEFRTTG (SEQ ID NO: 8), RNWRMSRRGGM (SEQ ID NO: 9), CVRGRGRMAGSV (SEQ ID NO: 10), ITRGELATVRRS (SEQ ID NO: 11), LRLGVGMGRTC (SEQ ID NO: 12), ERFAGNRNQLQ (SEQ ID NO: 13), GGLGSVGWYWA (SEQ ID NO: 14), GCGKERGRRALK (SEQ ID NO: 15), GQERLWAFRWVP (SEQ ID NO: 16), RGVLRVGTGRSE (SEQ ID NO: 17), ITRGELATVRRS (SEQ ID NO: 18), RPALRLGLIGPS (SEQ ID NO: 19), TRTSVDAPIRX (SEQ ID NO: 20), SKALRGVGSVAS (SEQ ID NO: 21) RRGQDRGHEPK (SEQ ID NO: 22), CLLGITCAIP (SEQ ID NO: 23), and a portion of any of these sequences. Alternatively, the bone-substitute scaffold is a synthetic compound, for example a polyethylene or a polycarbonate. In related embodiments, the amino acid sequence includes an amino acid analog, an amino acid derivative, or a conservative substitution of an amino acid residue.

In various embodiments, the peptide and the bone-substitute scaffold are non-covalently bound. Alternatively, the peptide and the bone-substitute scaffold are covalently bound. In an embodiment of the system, the peptide is linear. In an embodiment of the system, the peptide is circular. In an embodiment of the system, a portion of the peptide is linear and a portion of the peptide is circular.

An embodiment of the invention provides a method for identifying at least one compound having affinity for a eukaryotic cell receptor from a library of a plurality of compounds, the method including: contacting eukaryotic cells to a screening device including a supported porous mesh having a top surface and a bottom surface such that eukaryotic cells are contacted to the top surface, and the mesh has a pore size that retains the eukaryotic cells on the top surface and that permits passage of nutrient media and macromolecules, the device further forming a bottom compartment under the supported mesh with a container, for containing a fluid in communication with the mesh; and adding a sample of the library to the bottom compartment of the device in communication with the eukaryotic cells, and at least one compound binds with affinity to the cell receptor and is retained and recovered, and compounds are removed, thereby identifying the at least one compound.

In related embodiments prior to adding the sample, the method further includes culturing cells contacted to the top surface. Alternatively, the method further includes culturing cells on a surface separate from the porous mesh and then transferring and seeding the cells on the top surface of the mesh. In general, the library includes at least one compound selected from the group consisting of: a peptide, a protein, a lipid, a glycan, and a low molecular weight chemical compound. A "low molecular weight" compound means a drug-like compound having a molecular weight of less than about 1000.

In various embodiments, the eukaryotic cells are mammalian, for example the mammalian cells are of human origin. In related embodiments the eukaryotic cells include stem cells. For example, the stem cells are mesenchymal stem cells.

In related embodiments, the cells are derived from at least one tissue selected from: periodontal, ocular, epithelial, nerve, and endocrine.

In general, the method further includes identifying the compound bound to the receptor by at least one technique selected from: mass spectrometry, flow cytometry, and optical photometry.

In various embodiments, the compound is derived from a peptide recombinant genetic fusion in a prokaryotic display system encoding the plurality of compounds in a display library, and adding the sample includes contacting the eukaryotic cell with a portion of the display library.

In various embodiments, the prokaryotic display system includes bacteria or bacteriophage. For example, the bacteria include plasmids or prophage, and the bacteriophage include free filamentous phage virions or phage displayed bound to bacteria. In various embodiments, the molecule is characterized by a stimulatory activity for osteoblast cell differentiation. Alternatively, the molecule is characterized by stimulating osteoinduction and osteogenesis.

The term "osteoinduction", as used herein refers to the act or process of stimulating osteogenesis. The term "osteogenesis", as used herein refers the process of laying down new bone material by osteoblasts.

In various embodiments, adding the sample includes inverting the supported mesh such that cells retained on the mesh are in communication with library in the bottom compartment. In various embodiments, the method further includes identifying the peptide by isolating at least one display library clone bound to the eukaryotic cell, and obtaining a nucleotide sequence and deducing an amino acid sequence of the nucleotide sequence encoding the peptide. In a related embodiment, the method includes producing the peptide by expressing the recombinant fusion gene in bacterial cells. In an alternative embodiment, producing the peptide further includes synthesizing the amino acid sequence deduced from the nucleotide sequence. In various embodiments, the method further includes measuring affinity of peptide binding to an extracellular matrix (ECM) component.

In various embodiments, producing the peptide further includes isolating the strain encoding the peptide fusion on a solid nutrient medium to obtain genetic clones.

The method in various embodiments includes that the peptide is screened by iterative cycles of affinity selection and clonal amplification.

Another embodiment of the invention provides an amino acid sequence of a peptide identified by any of the methods herein.

An embodiment of the invention provides a system for biopanning including: a culture insert for a culture container, the insert includes lateral sides and a porous mesh supported in a plane substantially parallel to a bottom surface of the culture container, such that the porous mesh divides the lateral sides into at least one chamber, such that the mesh includes a pore size that retains eukaryotic cells and permits passage of a prokaryotic display system, such that the mesh includes a surface for adhesion and growth of the cell, and the insert further includes an outer diameter less than an inner diameter of the culture container.

In general, the system is sterilizable. In general, the insert is insertable and removable under sterile conditions with respect to the culture container. Alternatively, the insert is fixed and attached to the culture container.

In various embodiments, the insert including the porous mesh is invertible. In related embodiments, the system further includes cultured cells contacted to the porous mesh.

In various embodiments, the system provides a platform for cells, for example, cultured cells, but is also suitable for primary cells, contacted to porous mesh for adhesion and growth, on a platform in an insert having at least one chamber for growth. In an embodiment of the system in which the insert has a single chamber during the growth of cells, the insert is removed from the culture container, is inverted, and is wrapped circumferentially around the outer diameter of the insert to the mesh with Parafilm, such that the Parafilm wrapping forms a chamber above the inverted mesh platform. The height of Parafilm wrapping extends beyond the insert and forms a chamber for addition of the phage library. Parafilm is flexible, waterproof, semi-transparent, and moistureproof film that effectively seals labware or materials (Pechiney Plastic Packaging Company; Chicago, Ill.) and any material with similar properties is within the scope of the method and system herein.

In various embodiments of the system, the prokaryotic display system includes bacteria or bacteriophage having a library of recombinantly produced peptides, mutagenized by synthesis of nucleotides having a huge number of codons, prior to recombinant insertion into the operative cloning vector.

An embodiment of the invention provides a kit for identifying a molecule that has a specific affinity for binding to a eukaryotic cell receptor, the kit including the system according to systems described herein, a container for maintenance of sterility, and instructions for use.

In related embodiments, the kit further includes a prokaryotic display library or a chemical library. For example, the prokaryotic display library includes bacteria or bacteriophage.

BRIEF DESCRIPTION OF THE DRAWINGS

FIG. 1 is a set of drawings of a biopanning device for culturing osteogenic target cells on a porous mesh for contacting to a library.

FIG. 1 panel A is a drawing of a porous membrane, filter or mesh 101 supported across an internal lateral surface of a cylindrical insert 102. The terms membrane, filter and porous mesh are used interchangeably herein. The mesh has a pore size capable of maintaining target cells on the mesh and permitting passage of a library of molecules to access the target cells.

FIG. 1 panel B is a drawing showing the mesh 101 located transversely across a stage or platform within the cylindrical insert 102 that has an outer diameter narrower that a culture container 103. Osteogenic target cells 104 were inoculated onto the top surface of the mesh 101 located within the insert 102. The cells adhered to the mesh. The insert 102 was then placed in the sterile culture container 103 with cell culture medium 105. Growth was continued until confluence was obtained.

FIG. 1 panel C shows the insert 102 inverted for addition of the peptide-displaying bacterial cell library 106. The cells 103 following inversion of the insert 102 were located on the downward facing lower surface of the mesh 101.

FIG. 1 panel D shows addition of peptide-displaying bacterial cells 106 to a chamber above the mesh 101 located within the insert 102, to obtain binding of peptide-displaying bacterial cells 106 to the osteogenic target cells 104. The insert is cylindrical and located in the culture container 103 containing the culture medium 105. The bacterial cells displaying peptides 106 having amino acid sequences that bind to target cells 103 were identified and clones were expanded. Positive clones were isolated on agar plates as shown in Examples herein.

FIG. 2 is a set of drawing showing the biopanning device, and systems and methods for obtaining bacterial clones displaying peptides that bind to osteogenic cells.

FIG. 2 panel A shows a culture container 204 in which sterile osteogenic basal medium 203 (Lonza, Hopkinton Mass.) was placed in the lower compartment of the container 204. Osteogenic cells 205 were grown to confluence on the mesh 201 located transversely at the bottom of the cylindrical insert 202.

FIG. 2 panel B shows inversion of the insert 202 and with osteogenic cells 205 contacted and adhered to the mesh 201.

FIG. 2 panel C shows a wrapping of a flexible material 206, such as Parafilm, around the exterior lateral surface of the insert 202. The flexible material-wrapped insert forms a chamber or well having the mesh 201 as a floor or bottom of the chamber formed by the flexible material.

FIG. 2 panel D shows a peptide-displaying bacterial cell library 207 added to the chamber formed by the flexible material 206 wrapped around the insert 202. The insert 202 was placed into a culture container 204 with fresh medium 203. The bacterial cell library displays peptides that have amino acid sequences for selecting those having affinity for receptors on the osteogenic target cells 205. These peptides with affinity bound to the cells 205 on the mesh 201, while those that failed to bind did not.

DETAILED DESCRIPTION

Figure 3:
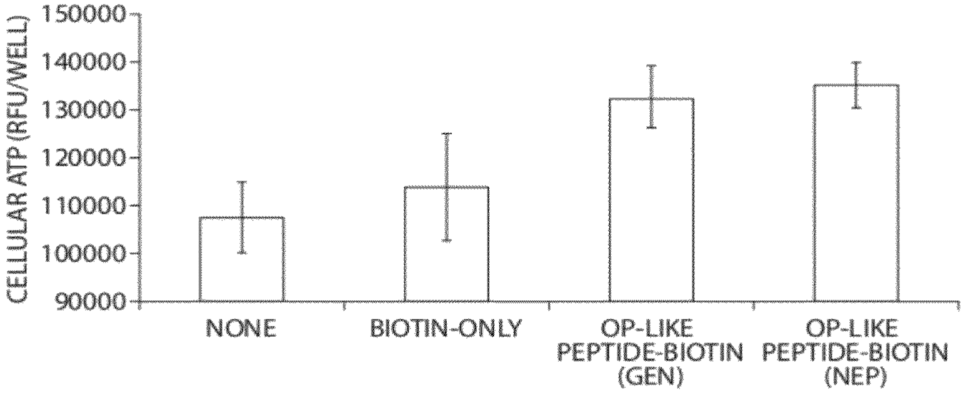
FIG. 3 is a bar graph showing cellular ATP amounts in MG63 cells (relative fluorescence units, RFU/well, ordinate) 24 hours after seeding and inoculating the cells into treated streptavidin-coated wells. Biotinylated peptides were synthesized by each of two commercial services, Genscript Inc. (GEN; Piscataway, N.J.) and New England Peptide, LLC (NEP; Gardner, Mass.). The wells were treated with in the following order from left to right (abscissa): control (none), biotin (biotin-only), biotinylated peptide synthesized by Genscript Inc. (OP-like peptide-biotin produced by GEN), and biotinylated peptide synthesized by New England Peptides LLC (OP-like peptide-biotin produced by NEP). The synthesized peptide had the following amino acid sequence ESHCLLGISCVL (SEQ ID NO: 6). The wells were washed, and MG63 cells (a human bone marrow derived stromal cell line) were added (1000 cells/well) to the wells. The height of the bars indicates amount of cellular ATP (ordinate) detected in the MG63 cells in each well. The data show that cells bound significantly more to the cells treated with peptide.

Bone is formed of calcified extracellular matrix (ECM), of which 70% is an inorganic calcium phosphate apatite. Bone apatite furnishes a scaffold for osteogenic cells, in which ECM proteins direct cells to differentiate into bone-forming osteoblasts. A bone grafting material is ideally composed of a scaffold structure and a source of ECM signals. However fundamental and technical limitations have prevented the development of an effective material. A critical disadvantage is a lack of complete information regarding active ECM signals. A few predominant, non tissue-specific ECM proteins have been identified, however the majority of bone ECM proteins, and the peptide sequences responsible for active signals of ECM proteins have not yet been fully characterized.

Devices and methods for identifying cells and cell receptors have generally used an immobilized protein, for example a purified immobilized protein, to obtain information about binding interactions and to determine ligands. The immobilized protein is purified away from the in vivo context and environment, and as a result has reduced or eliminated three-dimensional structural and functional characteristics of in vivo protein. This loss of in vivo structural and functional characteristics is a disadvantage that hinders accurate investigation into binding among cells and cell receptors. This limitation of current devices and methods is particularly pertinent for transmembrane proteins such as ECM receptor proteins.

Membrane proteins in vivo have a natural polarity that includes a set of protein surfaces directed into the cell and another set of protein surfaces that are exposed to the extracellular environment. The extracellular surfaces are generally hydrophilic. Membrane proteins further include a set of highly hydrophobic transmembrane regions. Proteins purified away from the membrane under conditions in which the hydrophobic regions are insoluble form micelles, and artificially adhere to irrelevant non-biological surfaces such as glassware and plasticware.

Therefore, as a result of artifacts and irreproducible results, there is a paucity of accurate information or inaccurate and incomplete information regarding the structure of ECM protein receptors. This lack of knowledge and information is a major barrier to investigating potential ligands of ECM protein receptors. These significant technical barriers stand in the way of developing lead compounds for new therapeutic agents.

The methods, systems and kits herein use a biopanning device for isolating of peptides having affinity for the cell, for example a live eukaryotic cell, in culture. The system and apparatus uses the living physiologically active cell as a target or bait.

Examples herein use a biopanning device (FIG. 1 and FIG. 2) with a culture insert 102 or 202 having a transverse mesh 101 or 201. The insert is insertable and removable, and consequently also is invertible. Inserts are commercially available in cylindrical form, however they may be manufactured in any geometrical shape convenient to a culture container 103 or 204, and are not limited by cross-sectional geometry. In general, the insert 102 or 202 is sterile or sterilizable, and the procedure is performed with sterile technique and sterile media and buffers. Methods for sterilizing the insert include autoclaving, baking, radiation and exposure of the insert to sterilizing gases. Examples herein utilize sterile cell culture equipment and microbiological procedures, for example, a sterile hood, or a sterile glove box, and sterile media and buffers. The inserts are manufactured from materials suitable for autoclaving such as a glass or a plastic, e.g., polycarbonate, polyethylene, isoprene, and Teflon. In various embodiments, the inserts and the culture containers have sterile covers.

Inserts have a smaller diameter to fit a variety of outer culture containers having a larger inner diameter. Inserts are singly or in a plurality used to obtain clonally distinct clones. Alternatively larger diameter inserts having a larger surface for growth of a larger number of target cells are useful to screen a larger number of clonally distinct members of the library to obtain a larger number of clones. Inserts have growth areas, for example, of at least about 4 $cm^2$, at least about 8 $cm^2$, at least about 20 $cm^2$, or at least about 50 $cm^2$.

A mesh 101 or 201 (FIG. 1 and FIG. 2) useful for the systems and methods herein is manufactured from any material which has a suitable pore size, and has surface properties that support adhesion and growth of eukaryotic cells. Pore size is sufficiently large to permit passage of bacteria, bacteriophage, and macromolecules. The pore size is for example at least about 3 microns (micrometers or μm) to about 8 microns, about 8 microns to about 20 microns, about 20 microns to about 40 microns, about 40 microns to about 60 microns, and about 60 microns to about 90 microns. The mesh or membrane is manufactured from a synthetic organic polymer material, for example hydrophilic polytetrafluoroethylene (PTFE), cellulose ester(s), polycarbonate, polyethylene, terepthalate, or cellulose acetate or other materials without limitation having similar characteristics.

The methods, systems and kits herein include pre-treating the mesh, for example, pre-rinsing the mesh to remove unwanted inorganic and organic substances from the membrane. These substances are often added to preserve or stabilize a membranous commercial product. Pre-treating the membrane improves eukaryotic cell viability, adhesion, and growth. Buffers include compounds for reducing non-specific binding of phage and bacterial cells to the membrane.

The methods, systems, kits and devices identify compounds having affinity for a eukaryotic cell receptor. The method shown in FIG. 1 and FIG. 2 involves contacting eukaryotic cells 104 or 205 to a mesh in the insert 102 or 202 such that cells are contacted to a "top" surface of mesh, i.e., the top being accessible to fluids that can be added and drained downwards by a gravitational force. Cells shown in FIGS. 1 and 2 illustrate the concept of the screen and are not to scale, as the cells have a diameter size of about 10 micron to about 100 micron diameter for eukaryotic cells, 1-4 microns for prokaryotic cells and are not visible to the naked eye. The cells are shown in FIGS. 1 and 2 to illustrate the principles of operation of the devices, methods, systems and kits herein. The pore size of the mesh 101 or 201 is selected so that the mesh retains the eukaryotic cells on the top surface and permits passage of prokaryotic library components and of nutrient media and macromolecules across the mesh.

The device further includes a bottom chamber, which is a well or a compartment that is formed under the supported mesh by the insert and the culture container floor, and which contains a fluid in communication with the mesh. The target cells seeded on top of the mesh are eukaryotic cells, for example osteogenic cells, cultured on the mesh until confluence is obtained. In the embodiment in FIG. 1, the insert 102 is inverted and a bacterial cell library displaying a peptide library 106 is added to the bottom chamber. In the embodiment in FIG. 2, an upper chamber is formed using a flexible material 206 wrapping such as Parafilm, and the peptide-displaying bacterial cell library 207 is added to the upper chamber.

The peptide-displaying bacterial cell library used herein is commercially available from Invitrogen (Carlsbad, Calif.). The Flitrx peptide display library catalog number K1125-01 contains random peptide dodecamer members (12mer). The theoretical total number of different amino acid sequences species is calculated as 20 (naturally occurring amino acids) to the $12^{th}$ power. The 200 million member library contains functional peptides including those having biological activity such as the function of an ECM ligand.

The FliTrx library displays peptides as a fusion protein of major bacterial flagellar protein (FliC) and thioredoxin (TrxA) on the surface of *E. coli* cells (Lu, Z. et al., 1995 Bio/Technology 13: 366-372). The library was engineered in the FliTrx plasmid (4970 bp). Thioredoxin-peptide fusions are displayed on the surface of *E. coli* cells by recombinantly inserting nucleotides encoding random dodecapeptides into the active site loop of the thioredoxin gene fused into a dispensable region of the flagellin gene (FliC). The peptide fusion construct is expressed from bacteriophage lambda major leftward promoter ($P_L$) which is an efficient high level promoter for bacterial expression (Buell, G. et al. 1986 Mechanism and Practice. In Maximizing Gene Expression, W. Reznikoff and L. Gold, eds. Boston, Mass.: Butterworth Publishers).

The induced fusion protein (FLITRX) is exported and assembled into flagella on the bacterial cell surface, displaying a constrained cyclic peptide at a sufficient distance from the bacterial cell to facilitate binding to a target receptor. Dodecamers are inserted within the thioredoxin active site loop, which constrains the N- and C-terminal ends of the peptide by a disulfide bond which protrudes from the fusion and is accessible to binding (Katti, S. K. et al., 1990 J. Mol. Biol. 212: 167-184). Expression of the cI repressor is regulated and engineered adjacent to the trp promoter in the *E. coli* host (GI826). Cells grown in tryptophan-free medium (IMC medium) transcribe the cI repressor gene, which binds to the $P_L$ promoter preventing transcription. Expression is induced by adding tryptophan to the medium allowing transcription from $P_L$ (Mieschendahl, M. et al. 1986 Bio/Technology 4: 802-808).

The Examples herein use as a target cells that are living and are physiologically active. The bait for identifying suitable peptide ligands is an in vivo plasma membrane including the ECM receptors of the cell. The methods herein consequently use as targets native three-dimensional cell membrane structures that bind the displayed peptides having amino acid sequences with affinity to the receptors. Receptors located on living cells present authentic in vivo signals as biopanning targets using the methods herein, which are suitable for isolation of peptides that serve as lead compounds to develop therapeutic agents to treat a variety of conditions, thereby facilitating drug development. The methods are not limited to isolation of ECM receptor ligands or osteogenic cells.

Peptide displaying phages were used and were inoculated in an inverted insert with a chamber having eukaryotic cells located on the opposite side of the mesh, i.e., the side opposite to the surface on which cells were grown on the mesh. Peptide ligands on the phage surface access and contacted ECM receptors on the eukaryotic cell basal plasma membrane by permeation into and across the pores of the mesh. The resulting affinity-selected peptide clones were isolated on an agar plate for secondary screening. Secondary screening identified specialized cell differentiation as a result of binding of the peptide. Clones inducing cellular differentiation were identified, and nucleotide sequences were determined to obtain the amino acid sequences of the selected peptides.

Phage display libraries and methods for identifying binding to molecules are shown for example in U.S. Pat. Nos. 5,096,815; 5,198,346; 5,223,409; 5,403,484; and 5,571,698 to Ladner et al., respectively. Phage display libraries and kits are commercially available including, for example Easy-MATCH™ Phage Display Library Screening Kit catalog number K1006-1 made by Clontech Inc. (Palo Alto, Calif.) and Phage Display Peptide Library Kit catalog number E8110S made by New England BioLabs Inc. (Ipswich, Mass.).

The commercially obtained bacterial cell library herein was designed to display peptides which are dodecamers, i.e, 12 amino acids in length. It was observed that the peptides obtained had amino acid sequences that were 11 amino acids and 12 amino acids in length. The mutagenesis procedure used to engineer the library and the recombinant methods involved in constructing the plasmid carrying the mutagenized DNA gave rise to clones of 11 and 12 amino acids in length.

The biopanning procedure and system is useful for a variety of types of cells including without limitation, periodontal tissues, eye lens, nerve, and endocrine tissues. The methods and systems are applicable to screening and identifying surface ligands that mediate, for example, cell-to-cell adhesion, and interconnection of various vertebrate systems, and maintenance of tissue integration, wound healing, cellular migration, and metastasis.

Furthermore, compounds that are screened with the target and bind to the target cells are not limited to peptides. The pore size of the mesh is traversed by small molecules, proteins, lipids, and glycans, and libraries of these types of compounds, which are analyzed using the methods, devices, systems and kits herein.

Examples herein identified peptides that support osteoblast cell growth and differentiation. Peptides are characterized by relative simplicity of large-scale synthesis, low cost, easy manufacturing and handling, direct presentation of the active signal, and high stability resulting in extended activity. A high-throughput bioassay system was developed and used in Examples herein to identity osteogenic peptides. Successive screenings were performed to select the peptides. Screening was performed to determine binding to ECM receptors on the pre-osteoblast basal cell surface, activity to stimulate cell growth and induction of osteoblastic marker alkaline phosphatase (AP). The clones bearing active peptides were sequenced, and an identified peptide having amino acid sequence ESHCLLGISCVL (SEQ ID NO: 6) was found having an amino acid sequence homologous to a portion of the amino acid sequence of osteopontin (OPN), a bone ECM protein. This osteopontin-like peptide was further analyzed and evaluated.

Peptides were synthesized by companies offering commercial peptide synthesis services utilizing fluorenylmethyloxycarbonyl (Fmoc) chemistry. Resins and methods for methods for synthesizing peptides using Fmoc schemes are shown for example in Webber et al. U.S. Pat. No. 5,563,220; and Evans et al U.S. Pat. No. 7,691,968. The peptides were synthesized using for example commercially available materials including Wang Resins (Anaspec Inc.; Fremont, Calif.), a Fmoc-Mini-PEG-COOH reagent (Peptides International Inc.; Louisville, Ky.), and a Fmoc-Lys(Bio)-OH reagent (Chem-Impex International Inc.; Wood Dale, Ill.). The peptides were cleaved, de-protected, and oxidized in water with contact with air. Purification of the cyclic peptides was performed, for example, with RP-HPLC.

Peptides identified herein further were synthesized and attached to biotin and polyethylene glycol (PEG) spacers. The water-soluble B-complex vitamin biotin (Vitamin $B_7$) is a well-known affinity material that binds avidin and streptavidin with very high affinity. Consequently, methods of labeling a molecule with biotin, i.e., biotinylation, to arrange for that molecule to be immobilized to a surface containing streptavidin include use of a spacer between the biotin from the molecule, using methods are known in the art, for steric purposes of functional access for binding of the molecule to a ligand (Huber et al., U.S. Pat. No. 5,521,319: Cosma, U.S. Pat. No. 6,150,123; and Schroder et al., U.S. Pat. No. 6,436,681). Biotin products and methods of biotinylating molecules are commercially available for example EZ-Link Biotinylation Kits product number 21425; Thermo Fisher Scientific Inc., Rockford, Ill., and CHROMALINK™-biotin-labeling-kit product number B-9007-105K; Solulink, Inc., San Diego, Calif.

Methods for synthesizing linear peptides and cyclic peptides are well known in the art of synthetic biochemistry. See for example Smythe et al., U.S. Pat. No. 7,589,170; Spatula et al U.S. Pat. No. 6,008,058. Linear and cyclic peptides herein were obtained from commercial services as indicated. Alternatively, peptides are synthesized by solid-phase methods (Barany et al. 1979 In: Gross et al., editors. The Peptides: Analysis, Synthesis, Biology. New York: Academic Press. Vol. 2: 1-284) using commercially available peptide synthesizers, for example Applied Biosystems Peptide Synthesizer (Foster City, Calif.), and products are purified for example using reverse-phase HPLC. Cyclic peptides containing disulfide-bridges are prepared, for example, peptides containing two cysteine residues in the amino acid sequence are oxidized using air or an iodine solution. The air oxidation is performed by continuously bubbling air overnight through the peptide in a dilute solution (100 ml, 0.015 lmol/ml) in aqueous ammonia pH 8.0 at 25° C. Aliquots are removed at time intervals and are analyzed by RP-HPLC. Polyethylene spacers, for example mini-PEG (Fmoc-8-amino-3,6-dioxaoctanoic acid; molecular weight 385.42), were used to derivatize peptides for addition of the substituted polyethylene glycol with a biotin.

The amino acids herein are indicated interchangeably by their name, one-letter symbol and three-letter symbol: alanine (A, ala); arginine (R, arg); asparagine (N, asn); aspartic acid (D, asp); cysteine (C, cys); glutamine acid (E, glu); glutamine (Q, gln); glycine (G, gly); histidine (H, his); isoleucine (I, ile); leucine (L, leu); lysine (K, lys); methionine (M, met), phenylalanine (F, phe); proline (P, pro); serine (S, ser); threonine (T, thr); tryptophan (W, trp); tyrosine (Y, tyr); and valine (V, val).

The term "derivative" of an amino acid means a chemically related form of that amino acid having an additional substituent, for example, N-carboxyanhydride group, a γ-benzyl group, an ε,N-trifluoroacetyl group, or a halide group attached to an atom of the amino acid.

The term "analog" means a chemically related form of that amino acid having a different configuration, for example, an isomer, or a D-configuration rather than an L-configuration, or an organic molecule with the approximate size and shape of the amino acid, or an amino acid with modification to the atoms that are involved in the peptide bond, to confer resistance to peptidases and proteases to a peptide.

The phrases "amino acid" and "amino acid sequence" include one or more components which are amino acid derivatives and/or amino acid analogs comprising part or the entirety of the residues for any one or more of the 20 naturally occurring amino acids indicated by that sequence. For example in an amino acid sequence having one or more tyrosine residues, a portion of one or more of those residues can be substituted with homotyrosine. Further, an amino acid sequence having one or more non-peptide or peptidomimetic bonds between two adjacent residues, is included within this definition.

Amino acids are classified into "groups" having chemically similar structures and chemical properties. The term "hydrophobic" amino acid means a group of aliphatic amino acids alanine (A or ala), glycine (G or gly), isoleucine (I or ile), leucine (L or leu), proline (P or pro), and valine (V or val), the terms in parentheses being the one letter and three letter standard code abbreviations for each amino acid, and a group of aromatic amino acids includes tryptophan (W or trp), phenylalanine (F or phe), and tyrosine (Y or tyr). These amino acids confer hydrophobicity as a function of the length of aliphatic and size of aromatic side chains in an amino acid sequence. The term "hydrophilic" amino acid means a group of amino acids including arginine (R or arg), asparagine (N or asn); aspartic acid (D or asp), glutamine acid (E or glu); glutamine (Q or gln), histidine (H, his), lysine (K or lys), serine (S or ser), and threonine (T or thr).

The term "neutral" amino acid means a group of amino acids including alanine (A or ala), asparagine (N or asn), cysteine (C or cys), glutamine (Q or gin), glycine (G or gly), isoleucine (I or ile), leucine (L or leu), methione (M or met), phenylalanine (F or phe), proline (P or pro), serine (S or ser), threonine (T or thr), tyrosine (Y or tyr), tryptophan (W or tip), and valine (V or val). The term "acidic" amino acid means a group of amino acids including aspartic acid (D or asp) and glutamic acid (E or glu). The term "basic" amino acids includes a group including arginine (R or arg), histidine (H or his), and lysine (K or lys).

The term "charged" amino acid means a group of amino acids including aspartic acid (D or asp), glutamic acid (E or glu), histidine (H or his), arginine (R or arg) and lysine (K or lys), which confer a positive (his, lys, and arg) or a negative (asp, glu) charge at physiological values of pH in aqueous solutions of peptides. The term "polar" amino acid means a group of amino acids including arginine (R or arg), lysine (K or lys), aspartic acid (D or asp), glutamine acid (E or glu), asparagine (N or asn), and glutamine (Q or gln).

Conservative substitutions of peptides herein include amino acid substitution of one or more amino acid residues with another amino acid from the same group. Peptides include one or more amino acid deletions or amino acid additions of amino acids internally or to the N-terminus and C-terminus.

Peptides were characterized functionally by several criteria. Cell number (i.e., proliferation), cell viability, and osteoblastic phenotype expression, such as osteocalcin and AP activity level (i.e., differentiation) resulting from treatment of cells with the peptides, and stability of each peptide were determined.

Histopathologic data including extent of bone formation, resorption, cortex formation, and fibrovascular tissue, and histomorphometrical data to assess bone regeneration capacity (e.g., height and area of bone defect and regeneration) are obtained in vivo assays. Delivery systems for the identified peptides and combinations of peptides and other molecules identified that stimulate effective osteogenic activity are known in the art of bone repair.

Synthetic materials are used as a platform for osteoblasts and stimulating molecules such as osteogenic peptides. Bone morphogenic proteins (BMPs) have limited ability to improve the osteogenic cell growth on apatite as a substrate. Numerous disadvantages of BMPs include rapid degradation of the large protein molecules, instability resulting in short half-life in the body, and difficulty in large scale synthesis of product resulting in low yields at a high cost. Despite complex significant osteogenic potential, peptides having functional characteristics of BMPs are not generally available as a complex with a synthetic bone material, for example apatite.

The apatite surface of bone is in dynamic equilibrium in vivo with calcium and phosphate ions frequently exchanged with environmental calcium and phosphate ions. Therefore, extent of ionic interactions between a peptide and apatite offers very limited basis for stable immobilization.

Treatment of non-union fractures, which are characterized by the failure of bone fracture fragments to unite and heal due to improper position of the broken bones, remains problematic. It is desirable to obtain improved grafting biomaterials such as the peptide-scaffold compositions herein.

Methods of screening herein utilize as a target a protein under in vivo conditions in which the protein presents multiple functional binding surfaces. Peptides obtained by the screening methods herein are bound to apatite by covalent binding or by physical mixing of the peptides and the apatite.

Multiple strategies to produce stable peptide-apatite compositions are available. Stable binding of peptide and apatite is achieved with pyrophosphate or polyphosphate covalently attached to the N-terminus of the peptide. These phosphate residues are easily linked to the N-terminus, and form multiple ionic bonds with calcium in apatite which are stable bonds. Improved apatite scaffolds and methods for optimizing additional scaffold materials including natural cancellous bone, demineralized natural cancellous bone, collagen, calcium phosphate, and hydroxyapatite are provided with peptides identified herein. Peptides are bound to scaffolds and are tested using in vitro and in vivo models, and result in materials having improved osteogenic activity. The peptides scaffolds are useful as therapeutic agents requiring osteogenic activity, for example, to promote bone formation, remodeling, and development.

Pharmaceutical Compositions

Pharmaceutical compositions are provided herein that include any of the peptides or other compounds isolated by methods herein, and optionally include a pharmaceutically acceptable carrier. Compositions optionally further include one or more additional therapeutic agents. Additional therapeutic agent or agents include growth factors, anti-inflammatory agents, vasopressor agents, collagenase inhibitors, topical steroids, matrix metalloproteinase inhibitors, ascorbates, angiotensin II, angiotensin III, calreticulin, tetracyclines, fibronectin, collagen, thrombospondin, transforming growth factors (TGF), keratinocyte growth factor (KGF), fibroblast growth factor (FGF), insulin-like growth factors (IGF), epidermal growth factor (EGF), platelet derived growth factor (PDGF), neu differentiation factor (NDF), hepatocyte growth factor (HGF), and hyaluronic acid.

As used herein, the term "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences Ed. by Gennaro, Mack Publishing, Easton, Pa., 1995 discloses various carriers used in formulating pharmaceutical compositions and known techniques for the preparation thereof. Examples of materials that are pharmaceutically acceptable carriers include but are not limited to, sugars such as glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, and other non-toxic compatible lubricants such as sodium lauryl sulfate and magnesium stearate, and coloring agents, releasing agents, coating agents, sweetening, flavoring and perfuming agents, preservatives and antioxidants can also be present in the composition, according to the judgment of the formulator.

Therapeutically Effective Dose

The growth and differentiation of osteogenic cells is promoted by contacting the sites in need of stimulation with a pharmaceutical composition as described herein. Thus shown are methods for treatment of bone or teeth defects including administering a therapeutically effective amount of a pharmaceutical composition including active agents that include at least one peptide herein or isolated by methods herein, to a subject in need thereof, in such amounts and for such time as is necessary to achieve the desired result, initiation or completion of bone healing. It will be appreciated that this encompasses administering the peptide or compound as a therapeutic measure to promote healing of a bone defect, or as a prophylactic measure to minimize complications associated with slow healing of a bone defect, e.g., as an irrigation solution during and following bone surgery.

As used herein, the "therapeutically effective amount" of the pharmaceutical composition is that amount effective for promoting growth or re-growth of bone. The composition, according to the methods herein, is administered using an amount and a route of administration effective for healing a bone defect. Thus, the expression "amount effective for promoting healing of a bone defect", as used herein, refers to an amount of the composition sufficient to cause deposition of new bone by stimulation of growth, replication and differentiation of osteogenic stem cells into osteoblast cells. The exact dosage is chosen by the individual physician in view of the patient to be treated. Dosage and administration are adjusted to offer sufficient levels of the active agent(s) or to maintain the desired effect. Additional factors which may be taken into account include the severity of the disease state, e.g., size and location of the bone defect; age, weight and gender of the patient; diet, time and frequency of administration; drug combinations; reaction sensitivities; and tolerance/response to therapy. Long acting pharmaceutical compositions might be administered every 3 days to 4 days, every week, or once every two weeks depending on half-life and clearance rate of the particular composition.

The active agents are preferably formulated in dosage unit form for ease of administration and uniformity of dosage. The expression "dosage unit form" as used herein refers to a physically discrete unit of active agent appropriate for the patient to be treated. It will be understood, however, that the total daily usage of the compositions will be decided by the attending dentist, oral surgeon or physician within the scope of sound medical judgment. For any active agent, the therapeutically effective dose is estimated initially either in cell culture assays or in animal models, usually mice, rabbits, dogs, or pigs. The animal model is also used to achieve a desirable concentration range and route of administration. Such information can then be used to determine useful doses and routes for administration in humans. A therapeutically effective dose refers to that amount of active agent which ameliorates the symptoms or condition. Therapeutic efficacy and toxicity of active agents are determined by standard pharmaceutical procedures in cell cultures or experimental animals, e.g., ED50 (the dose is therapeutically effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions which exhibit large therapeutic indices are preferred. The data obtained from cell culture assays and animal studies are used in formulating a range of dosage for human use.

Administration of Pharmaceutical Compositions

After formulation with an appropriate pharmaceutically acceptable carrier in a desired dosage, the pharmaceutical compositions are administered to humans or to other mammals generally following a surgical procedure to access proximity to the bone defect, depending on the severity and location of the bone defect being treated.

Liquid dosage forms for oral surgery include, but are not limited to, pharmaceutically acceptable emulsions, microemulsions, solutions, suspensions, syrups and elixirs. In addition to the active agent(s), the liquid dosage fauns may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

The active agent is admixed under sterile conditions with a pharmaceutically acceptable carrier and any needed preservatives or buffers as may be required. For example, bone defects located proximal to eyes, nose, and jaw may be treated with aqueous drops, a mist, an emulsion, or a cream. Administration may be therapeutic or it may be prophylactic. Prophylactic formulations may be present or applied to the site of potential bone defects, or to sources of bone defects, such as oral surgery or rhinoplasty and other procedures affecting appearance of the face. Included are ophthalmological devices, surgical devices, audiological devices or products which contain disclosed compositions (e.g., gauze bandages or strips), and methods of making or using such devices or products. These devices may be coated with, impregnated with, bonded to or otherwise treated with a disclosed composition.

The ointments, pastes, creams, and gels may contain, in addition to an active agent, excipients such as animal and vegetable fats, oils, waxes, paraffins, starch, tragacanth, cellulose derivatives, polyethylene glycols, silicones, bentonites, silicic acid, talc, zinc oxide, or mixtures thereof.

Powders and sprays can contain, in addition to the agents, excipients such as talc, silicic acid, aluminum hydroxide, calcium silicates, polyamide powder, or mixtures of these substances. Sprays can additionally contain customary propellants such as chlorofluorohydrocarbons.

The sterile injectable preparation may be a sterile injectable solution, suspension or emulsion in a nontoxic acceptable diluent or solvent, for example, as a solution in 1,3-butanediol. Among the acceptable vehicles and solvents that are employed are water, Ringer's solution, U.S.P., and isotonic sodium chloride solution. In addition, sterile, fixed oils are conventionally employed as a solvent or suspending medium. For this purpose any bland fixed oil is employed including synthetic mono- or diglycerides. In addition, fatty acids such as oleic acid are used in the preparation of injectables. The injectable formulations are sterilized, for example, by filtration through a bacterial-retaining filter, or by incorporating sterilizing agents in the form of sterile solid compositions which can be dissolved or dispersed in sterile water or other sterile injectable medium prior to use. Delayed absorption of an administered active agent to reduce loss of bone proximity by diffusion may be accomplished by dissolving or suspending the agent in an oil vehicle. Injectable depot forms are made by forming microencapsulation-matrices of the agent in biodegradable polymers such as polylactide-polyglycolide. Depending upon the ratio of active agent to polymer and the nature of the particular polymer employed, the rate of active agent release can be controlled. Examples of other biodegradable polymers include poly(orthoesters) and poly(anhydrides). Depot injectable formulations are also prepared by entrapping the agent in liposomes or microemulsions which are compatible with body tissues adjacent to the bone defect.

Release controlling coatings and other coatings are well known in the pharmaceutical formulating art. In such solid dosage forms the active agent(s) may be admixed with at least one inert diluent such as sucrose or starch. Such dosage forms may also include, as is normal practice, additional substances other than inert diluents, e.g., tableting lubricants and other tableting aids such a magnesium stearate and microcrystalline cellulose. The dosage forms may also contain buffering agents. The dosage forms may optionally contain opacifying agents and can also be of a composition that they release the active agent(s) only, or preferentially, in a certain part of the intestinal tract, optionally, in a delayed manner. Examples of embedding compositions which can be used include polymeric substances and waxes.

Uses of Pharmaceutical Compositions

As discussed above and described in greater detail in the Examples, peptides isolated by devices, methods, systems, and kits herein are useful as stimulators of growth and development of cells and tissues involved in bone formation. Without being limited by any particular theory or mechanism of action, compounds herein such as peptides are capable of function on a large range of cell types, for example, to stimulate healing bone defects, for example, bones of the jaw having defects associated with progressive gum diseases and tooth loss. The peptides herein bind to receptor proteins associated with the ECM receptors in a variety of tissues and cells, including cartilage and chondrogenic cells.

Peptides herein may further be used to stimulate bone re-growth under physiological conditions of bone loss such as osteopenia and osteoporosis. These conditions are increasingly found in aging populations particularly in temperate climates in which vitamin D seasonally limits extent of bone formation and bone metabolism is consequently shifted to osteoclastic bone destruction. Alternatively, peptides herein are effective in increasing incorporation of bone grafts following surgery to reconstruct bones after traumatic events such as collisions and war injuries. Suitable bone grafts include, but are not limited to autografts, artificial bone grafts, allografts, delayed grafts, full thickness grafts, heterologous grafts, xenografts, homologous grafts, and hyperplastic grafts.

The methods, kits, and systems encompassed herein are therapeutic for treating bone wounds and defects in humans, and to treat other mammals including without limitation bovine, canine, feline, caprine, ovine, porcine, murine, and equine species.

The methods and kits now having been described are exemplified by the following examples and claims, which are exemplary only and are not intended to be construed as further limiting. The contents of all of the references cited are hereby incorporated herein by reference.

EXAMPLES

Example 1

Multiple Biopanning Devices and Methods

Biopanning devices and systems shown in FIG. 1 have a cell culture insert 102 having two compartments, an upper compartment and a lower compartment separated by a platform which includes a mesh 101 having about five micron to about ten micron pore size (FIG. 1 panel A). Culture inserts are commercially available in a variety of pore sizes and diameters (Millipore Corp., Billerica, Mass.; and BD Falcon, Franklin Lakes, N.J.). The five to ten micron pore size retains eukaryotic cells and permits passage of bacteria and bacteriophage library members.

The insert 102 was placed in a culture container 103. Culture medium 105 was added to the culture container 103. Osteogenic target cells 104 having ECM were grown to confluence on the surface of the mesh 101 in the upper compartment of the insert 102. The resulting confluent cells adhered to the surface of the mesh 101. The confluent cultured ECM cells were observed to have normal eukaryotic cell properties (FIG. 1 panel B).

The culture insert 102 was inverted such that the bottom surface of the mesh 101 upwardly faced the apical opening of the container 103 (FIG. 1 panel C). The surface of the mesh 101 with adhering confluent cells faced the bottom of the container 103 following the inversion. A peptide-displaying bacterial cell library 106 is added to the surface of the mesh 101 facing the apical opening (FIG. 1 panel D).

A biopanning device shown in FIG. 2 has a cell culture insert 202 with a single chamber or compartment. The porous mesh 201 was located at a bottom or floor of the compartment, parallel and in contact with the bottom or floor of the culture container 204. The single compartment is formed from the insert 202 having a closed end and an open end, with the closed end of the insert 202 having the mesh 201. The mesh is permeable, however is placed on the floor of the culture container as illustrated in FIG. 2 panel A. The insert 202 was placed into the culture container 204. Cells 205 were contacted to and cultured on the upper surface of the mesh 201 in cell culture medium 203 which was added to the container 204 for standard culture of cells 205 (FIG. 2 panel A).

The cells 205 were cultured and cell adherence to the surface of the mesh 201 and confluence were obtained. The insert 202 was removed from the container 204, was inverted (FIG. 2 panel B), and the flexible material 206 Parafilm was wrapped around the insert 202 to extend above and below the horizontal level of the porous mesh 201 located within the insert 202. The original upper surface of the mesh 201 having adhered confluent cells 205 was inverted to a position facing downward following inversion, and the surface of the mesh 201 not contacted with cells with flexible material 206 wrapping formed an additional compartment for a bio-panning well above the mesh (FIG. 2 panel C). The insert 202 was placed into a container with fresh culture medium 203. A portion of a peptide-displaying bacterial cell library 207 was added to the additional compartment formed by the flexible material 206 having the surface of the mesh 201 that was opposite to the surface having confluent cells 205 (FIG. 2 pane D). The library members permeate the mesh 201, contact the adhered eukaryotic target cells 205, and those bacterial cells bearing peptides having affinity for cell receptors were retained on the target cells.

Example 2

Cells, Inserts, and Cell Culture Medium

The hMSC cells from human bone marrow are commercially available (Lonza; Allendale, N.J.). An insert having a mesh was obtained from BD Falcon (Franklin Lakes, N.J.). The mesh was made of polyethylene terephthalate (PET) with eight micron pore size and 0.3 $cm^2$ cell growth area. Mesh sizes and pore sizes of other dimensions are also suitable. Eighty-thousand cells were seeded on the mesh and were cultured in osteogenic basal medium (Lonza; Allendale, N.J.) supplemented with 10% fetal bovine serum (FBS; FIG. 2 panel A). After three days of culture, the cells formed a confluent monolayer.

Example 3

Peptide Displaying Bacterial Cell Library

A vial containing $2\times10^{10}$ cfu/ml of a commercially available peptide-displaying bacterial cell library (Flitrx peptide display library; Invitrogen, Carlsbad, Calif.) was diluted into 50 ml tryptophan-free IMC medium (Flitrx panning kit, Invitrogen) containing 100 μg/ml of ampicillin, ($IMC^{amp}$ medium). Bacterial cells were incubated at 25° C. overnight with shaking at 250 rpm, and $10^{10}$ cells were re-suspended in 50 ml fresh $IMC^{amp}$ medium supplemented with 100 μg/ml of tryptophan, and were grown at 25° C. with shaking for six hours for induction of peptide expression. Cell concentration was determined by optical density at 600 nm.

Example 4

Biopanning Using Peptide-Displaying Bacterial Cells

Bacterial cells displaying peptides as grown above ($10^9$ cells/ml) were re-suspended in 50 mM Hepes buffer pH 7.5, with 1% nonfat dry milk, 146 mM NaCl, 4 mM KCl, 1 mM $CaCl_2$, 0.5 mM $MgCl_2$, 5 mM glucose and 1% a-methylmannoside.

The culture insert was inverted and the surface that previously formed the bottom of insert was wrapped with Parafilm to form a culture space above the mesh in the newly formed chamber opposite the side of the mesh with the adhered target hMSC cells (FIG. 2 panels B and C). Two hundred microliters of the peptide-displaying bacterial suspension ($2\times10^8$ cells containing approximately one copy of each clone) were incubated in the chamber above the hMSC cells for 5 minutes with gentle rocking (FIG. 2 panel D). The hMSC target cells remained adhered to the inverted mesh surface and library members circulated throughout the mesh to the target cells.

Following incubation to select for clones that bound the target, the mesh surface was washed with suspension buffer three times to remove unbound library members. Bacterial cells that were specifically bound to hMSC cells were removed by adding $IMC^{amp}$ medium to the mesh and vortexing. Bacterial cells were grown and expanded overnight at 25° C. with shaking at 250 rpm.

Serial dilutions of resulting clones were spread on RMG ampicillin agar plates (Flitrx panning kit; Invitrogen) to obtain appropriate numbers of bacterial clone colonies per plate. Ninety-five bacterial colony clones were obtained, and each was transferred to 100 μl of IMC medium in a 96-well plate. The parental strain of bacteria containing the control empty vector plasmid was inoculated in a control well. Clones were grown overnight in the medium, and expression of the peptides displayed on each clone was induced by addition of tryptophan and growth for six hours.

Example 5

Secondary and Tertiary Screening of Bacterial Clones

A secondary screen of clones bearing peptides was designed to determine activity of these peptides. Osteoblast progenitor cells differentiate into mature osteoblasts to produce bone in a multi-step process including: migration of cells to a bone surface, resulting in exposure of bone ECM protein active sequences to osteoclast activity; differentiation into osteoblasts; osteoblast replication; and expression of osteoblast marker genes, such as type I collagen and alkaline phosphatase, following signaling by a component of ECM. The screening parameter chosen was growth of mesenchymal stem cells, because cell replication is an early function of osteoblast progenitor cells. Physiological measures of active cell growth include increased cellular content of ATP, increased cellular respiration and DNA synthesis.

Cells growth was analyzed using a commercially available assay that measures cellular ATP content in as few as 50 cells (CellTiter Glo ATPase assay; ProMega, Madison, Wis.). A reagent for this assay was added directly into the cell culture and luminescence in homogeneous assay mode was detected.

A tertiary screen of the identified peptides was performed. The effect of each peptide on target cells was determined by measuring amounts of osteoblastic marker alkaline phosphatase (AP). Clonally purified individual isolates, or sibling pools of multiple isolates, were tested using the secondary and tertiary screens.

Individual preparations of each bacterial peptide-bearing clone to be tested were induced to express peptides, and were heat-devitalized in boiled water, to kill the peptide-displaying bacteria. Fifty microliters of heat-devitalized bacterial suspension was poured into each well of a 96-well plate containing agar, and the plate was centrifuged at 2000 rpm to embed bacteria in the surface of the agar.

The hMSC cells do not grow or replicate on agar, therefore an increase in hMSC cell metabolism, as measured for example by ATP content, would be observed only upon contact with a specific functional peptide to an ECM receptor located on the hMSC cell and stimulation and support of growth of the cell.

hMSC cells in osteogenic basal medium with 10% FBS were seeded (20,000 cells/well) onto the plate having clone-embedded agar wells, and cell growth was quantified by ATP content 72 hours after seeding using a commercially available kit, CELL TITER-GLO™ Luminescent Cell Viability Assay (Promega; Madison, Wis.).

Example 6

Identification of Osteoinductive Peptide Sequence

Selected clones were expanded and DNA was isolated. Each clone was grown at 30° C. overnight in 100 μg/ml ampicillin containing RM medium (Flitrx kit, Invitrogen Inc.). DNA was isolated (S.N.A.P. Miniprep kit; Invitrogen, Carlsbad, Calif.) for DNA sequencing, and an amino acid sequence of the peptide displayed on each clone was determined from the DNA sequence. DNA was sequenced using a reverse sequencing primer: TAGCATCGTCCAGCGCTTTC (SEQ ID NO: 25; Seqwright Inc., Houston Tex.). Aliquots of each clone were preserved at 80° C. in glycerol.

Example 7

Cellular ATP Analysis of Cells Contacted with Clones

Osteoblast progenitor cells were seeded on the agar plates seeded with the heat-devitalized clones. The growth of the osteoblast cells was observed by measuring amount of cellular ATP after appropriate incubation (Table 1). Control ATP was measured in a well having cells treated with an empty vector control clone (position A1, Table 1). Specific clones located at positions F10, G3, G4, G5 and H8 were observed to produce significantly greater luminescence than this control. Clones contained 5.8, 10.7, 10.3, 5.9, and 6.9-fold, respectively, more ATP than the control.

These and other bacterial clones that displayed peptides which greatly stimulated osteoblast precursor cells were thus identified by selecting those resulting in the highest relative ATP luminescence units, to be further characterized.

Example 8

Identification of Peptide Sequences

Clones were further tested to quantify amount of stimulation of alkaline phosphatase (AP) activity in contacted cells. One clone was observed to result in an order of magnitude more AP expression than that of control cells contacted with empty vector. DNA from this clone that stimulated AP expression was isolated and was sequenced, and the DNA sequence was used to obtain amino acid sequence VFLRGNNSGGRS (SEQ ID NO: 2). This amino acid sequence appears not to have been previously reported.

Data analysis of the sequence showed the presence of tripeptides RGN and GGR, which are tripeptides associated with osteoinduction. Isolation of a bacterial clone encoding this dodecamer sequence demonstrates success of the methods herein.

Example 9

Sequencing of Peptides

Additional screening identified further clones having amino acid sequences that induced osteoblastic marker enzyme alkaline phosphatase. Osteoinductive peptides with activity that stimulated osteoblasts include: VFLRGNNSGGRS (SEQ ID NO:2), GKIHRHRGQAVE (SEQ ID NO: 3), HIRQMPVRAGLS (SEQ ID NO: 4), RQGVGSNGXIQK (SEQ ID NO: 5), ESHCLLGISCVL (SEQ ID NO: 6), QQLQQNVILET (SEQ ID NO: 7), RSKLVEFRTTG (SEQ ID NO: 8), RNWRMSRRGGM (SEQ ID NO: 9), CVRGRGRMAGSV (SEQ ID NO: 10), ITRGELATVRRS (SEQ ID NO: 11), LRLGVGMGRTC (SEQ ID NO: 12), ERFAGNRNQLQ (SEQ ID NO: 13), GGLGSVGWYWA (SEQ ID NO: 14), GCGKERGRRALK (SEQ ID NO: 15), GQERLWAFRWVP (SEQ ID NO: 16), RGVLRVGTGRSE (SEQ ID NO: 17), ITRGELATVRRS (SEQ ID NO: 18), RPALRLGLIGPS (SEQ ID NO: 19), TRTSVDAPIRX (SEQ ID NO: 20), SKALRGVGSVAS (SEQ ID NO: 21), and RRGQDRGHEPK (SEQ ID NO: 22).

Amino acid sequence of a peptide isolated herein ESHCLLGISCVL (SEQ ID NO: 6) was observed to share homology with a portion of osteopontin, which is a cell-binding sialoprotein specific to bone. In addition, a peptide bearing a direct amino acid sequence of osteopontin CLLGITCAIP (SEQ ID NO: 23) was synthesized for control purposes.

Example 10

Synthesis of Cyclic and Linear Forms of SEQ ID NO: 6

Peptide ESHCLLGISCVL (SEQ ID NO: 6) was synthesized in each of a linear form and a cyclic form. The growth supporting and differentiation inducing activities of the peptide were determined using osteoblastic cells.

The synthesized peptide preparations were PEGylated to improve water solubility and to reduce steric hindrance between the biotin and peptide; and were biotinylated to facilitate immobilization on streptavidin assay surfaces. Peptides were synthesized by each of two commercial services, Genscript Inc. (Piscataway, N.J.) and New England Peptide, LLC. (Gardner, Mass.).

Peptides synthesized by Genscript Inc. (GEN) and New England Peptide LLC (NEP) contained different sizes of polyethylene glycol (PEG). Peptides made by GEN contained three repeats of commercially available mini-PEG (Fmoc-8-amino-3,6-dioxaoctanoic acid; Peptides International, Louisville, Ky.). Peptides made by NEP contained commercially available 15 atom-PEG (Merck Biosciences, Darmstadt, Germany) respectively.

biotinylated peptides than in cells inoculated into wells treated with buffer only, and compared to cells in wells treated with biotin only (FIG. 3). Cells inoculated into wells treated with biotinylated peptides produced about three-fold to four-fold more ATP than biotin-only (subtracted for background).

Peptide preparations synthesized by NEP were observed to stimulate greater cellular ATP amounts than biotinylated peptides synthesized by GEN, although the difference at 24 hours was less than about 15%.

Figure 4:
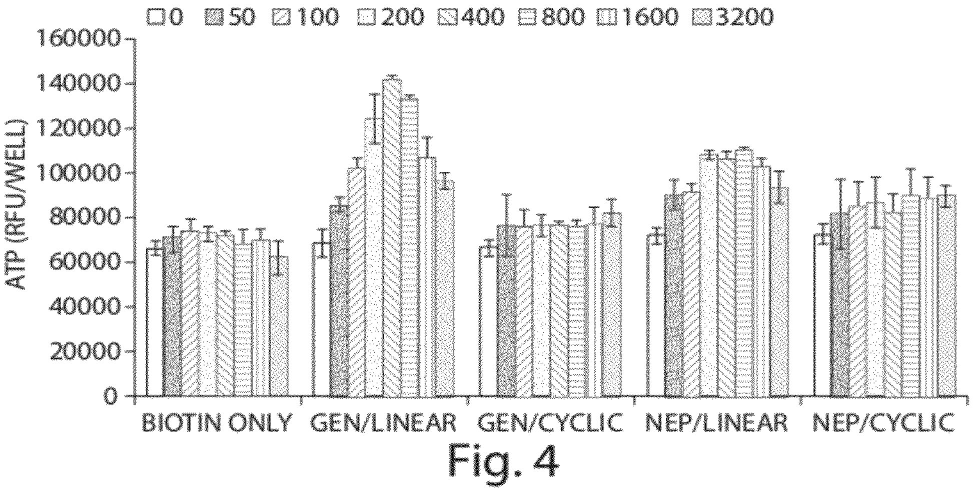
FIG. 4 is a bar graph showing cellular ATP amounts (relative fluorescence units, RFU/well, ordinate) in MG63 cells 120 hours after inoculating the cells into treated streptavidin-coated wells. Prior to adding cells, wells were treated with serial dilutions of biotin samples with or without a cyclic or a linear form of peptide having amino acid sequence ESHCLLGISCVL (SEQ ID NO: 6) produced by GEN or NEP respectively. Serial dilutions of samples were prepared: 50 pmole/well, 100 pmole/well, 200 pmole/well, 400 pmole/well, 800 pmole/well, 1600 pmole/well, or 3200 pmole/well. The samples were added to the streptavidin-coated well is in the following order from left to right (abscissa): biotin (biotin-only); biotinylated linear peptide synthesized by GEN (GEN/linear); biotinylated cyclic peptide synthesized by GEN (GEN/cyclic); biotinylated linear peptide synthesized by NEP (NEP/linear); or biotinylated cyclic peptide synthesized by NEP (NEP/cyclic). The wells were washed to remove unbound sample and cells were then inoculated into the wells (1,000 cells/well). The height of the each bar indicates amount of cellular ATP observed in cells in response to amount of peptide. The biotinylated peptides in FIG. 3 and FIG. 4, regardless of source of synthesis, stimulated ATP production and cellular growth of the cells at each time point tested, i.e., 24 hours and 120 hours after seeding.

Greater cell growth was observed at 120 hours after seeding of cells inoculated into wells treated with biotinylated linear peptides than wells treated with biotinylated cyclic peptides, independent of the source of the synthesis (FIG. 4).

Cells in wells treated with linear peptides synthesized by GEN produced greater ATP amounts than those in wells treated with any of the other peptides, and the biotin only control. The observed differences in ATP amounts between the GEN synthesized peptides and NEP synthesized peptides were not significant considering the coefficients of variation of titrations. Thus, data show that the biotinylated peptides, regardless of source of synthesis, stimulated ATP production and cellular growth at each time point tested (i.e., 24 hours and 120 hours after seeding).

Greater ATP amounts were observed in wells having 200, 400, 600, or 800 pmole/well of peptide, independent of the source of the peptide than at 50, 100, 1600 or 3200 pmole/well, for both linear and cyclic peptides (FIG. 4).

TABLE 1

Cellular ATP (relative luminescence per cell) in cells stimulated by selected peptide-displaying bacterial clones.

| | 1 | 2 | 3 | 4 | 5 | 6 | 7 | 8 | 9 | 10 | 11 | 12 |
|---|---|---|---|---|---|---|---|---|---|---|---|---|
| A | 7,075 | 3,335 | 3,550 | 2,955 | 3,765 | 3,880 | 3,715 | 5,935 | 3,240 | 2,415 | 4,630 | 4,050 |
| B | 9,245 | 7,300 | 4,160 | 2,380 | 3,035 | 3,530 | 2,800 | 3,470 | 2,325 | 2,820 | 3,360 | 2,930 |
| C | 3,105 | 2,505 | 5,255 | 2,885 | 3,455 | 2,905 | 4,140 | 2,540 | 2,425 | 2,140 | 2,270 | 2,590 |
| D | 5,425 | 3,740 | 16,430 | 4,135 | 3,835 | 3,865 | 3,380 | 3,650 | 3,775 | 4,160 | 3,555 | 6,195 |
| E | 3,495 | 4,870 | 18,270 | 6,205 | 6,710 | 5,385 | 3,600 | 5,605 | 6,040 | 5,785 | 5,655 | 5,560 |
| F | 5,540 | 7,790 | 7,780 | 8,760 | 8,550 | 6,145 | 4,530 | 5,290 | 8,410 | 40,665 | 16,200 | 6,480 |
| G | 8,335 | 10,945 | 75,455 | 72,525 | 41,385 | 9,055 | 5,965 | 6,810 | 8,070 | 11,615 | 7,905 | 26,700 |
| H | 4,320 | 6,199 | 8,356 | 3,870 | 9,063 | 8,993 | 8,890 | 48,890 | 39,150 | 8,745 | 39,530 | 8,570 |

Example 11

Cyclic and Linear Forms of SEQ ID NO: 6 Induced Cell Growth and AP Activity

Cell growth and osteogenic inducing potential of each of the preparations of the biotinylated linear and the cyclic peptides was determined. The osteogenic potential of each peptide was analyzed by quantifying cellular ATP and alkaline phosphatase (AP) activity of osteoblast cells.

Peptides were added to the wells in titrated amounts (50 pmole/well, 100 pmole/well, 200 pmole/well, 400 pmole/well, 800 pmole/well, 1600 pmole/well, or 3200 pmole/well) and were immobilized on streptavidin-coated plastic well plates (384 wells per plate). The biotin-binding capacity of the plates was 50 pmole/well. Each well was washed to remove unbound biotinylated peptides. Human bone marrow derived stromal cell line of MG63 cells (1,000 cells/well) were inoculated into each well.

ATP (RFU/well) was measured at each of 24 hours and 120 hours after cells were seeded, and alkaline phosphatase (AP, RFU standardized by cell number) activity was measured 120 hours after cells were seeded.

Figure 5:
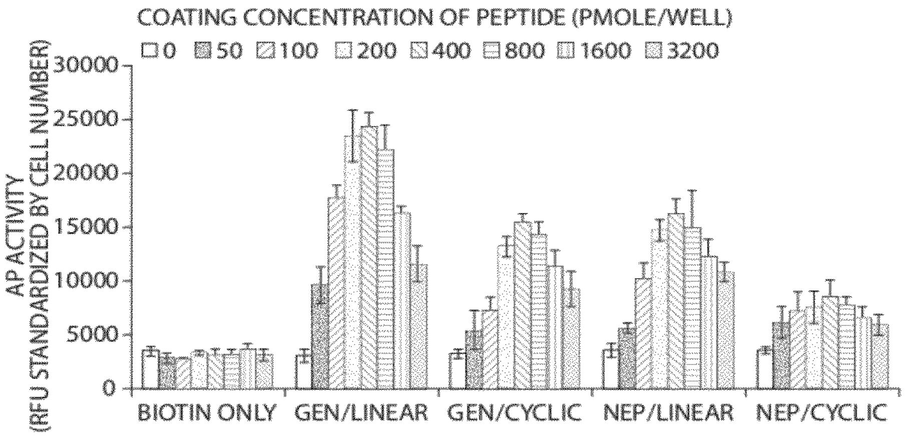
FIG. 5 is a bar graph showing MG63 cell alkaline phosphatase activity (AP activity in RFU units, ordinate) 120 hours after seeding cells into treated streptavidin-coated wells. The wells were treated with a cyclic or a linear form of a peptide having amino acid sequence ESHCLLGISCVL (SEQ ID NO: 6) produced by each of synthesis companies GEN and NEP respectively, or controls. Serial dilutions of the peptides were prepared to contain: 50 pmole/well, 100 pmole/well, 200 pmole/well, 400 pmole/well, 800 pmole/well, 1600 pmole/well, or 3200 pmole/well. Peptides or controls were added to the streptavidin-coated well in the following order from left to right (abscissa): biotin (biotin-only); biotinylated linear peptide synthesized by GEN (GEN/linear); biotinylated cyclic peptide synthesized by GEN (GEN/cyclic); biotinylated linear peptide synthesized by NEP (NEP/linear); or biotinylated cyclic peptide synthesized by NEP (NEP/cyclic). The wells were washed to remove unbound peptides or controls. Cells were inoculated into the wells (1,000 cells/well). Amount of cellular alkaline phosphatase produced by the cells is indicated on the ordinate. Data show that the biotinylated linear peptides and biotinylated cyclic peptides induced greater alkaline phosphatase activity than the controls, and that at each amount the linear peptide was more stimulatory than the cyclic peptide.

Greater ATP amounts and cell growth were observed at 24 hours after seeding in cells inoculated into wells coated with The biotinylated linear and cyclic peptides stimulated greater AP activity at 120 hours after seeding than biotin alone (FIG. 5). Greater AP activity was produced by cells in wells having linear peptides compared to corresponding cyclic peptides synthesized by each company. The highest AP activity was observed in wells treated with 200, 400, 600, or 800 pmole/well of biotinylated peptides.

Differences in AP production were observed in cells treated with biotinylated peptides synthesized by GEN and NEP. Peptides synthesized by GEN resulted in greater AP activity than peptides synthesized by NEP.

Data show that both linear and cyclic peptides having amino acid sequence ESHCLLGISCVL (SEQ ID NO: 6) induced cell growth and production of osteogenic marker AP in MG63 cells.

Example 12

Synthesis of Osteoinductive and Osteogenic Peptides

Peptides isolated and identified herein having amino acid sequences (SEQ ID NO: 2) through (SEQ ID NO: 22) were chemically synthesized in linear and cyclic form to evaluate osteogenic activity of each. Control synthetic peptides include: GTPGPQGIAGQRGVV (SEQ ID NO: 24) a commercially available peptide PepGen P-15 (Friddent GmbH, Dentsply, UK), commercially available tripeptide RGD, and control peptides CLLGITCAIP (SEQ ID NO: 23) having amino acid sequence of residues 9-18 of human osteopontin, NSVNSKIPKACCVPTELSAI (SEQ ID NO: 26) having amino acid sequence of residues 68-87 of BMP-2, and GTPGPQGIAGQRGVV (SEQ ID NO: 27) having amino acid sequence of residues 766-780 of type I collagen.

The osteoinductive peptides screened and identified in Examples herein having functional capacity to bind to cells, were isolated as a fusion protein attached to structural components of the bacterial cell (i.e., flagellar protein). The context of fusion to the protein FliC may improve water solubility of hydrophobic peptides. To enhance solubility of resulting peptides, hydrophilic PEG is linked to the synthetic peptide to improve water solubility. The chain length of PEG is indicated by n, such that n is a whole number such as 1, 2, 3, 4, . . . 8, . . . 12, . . . or 24. The chain length of PEG is optimized for each linear or cyclic sequence hydrophobic peptides.

The PEGylated-peptides are biotinylated on either the N- or C-terminus of each peptide. The free terminal end (i.e., either the N-terminus or the C-terminus) is methylated or is amidated to protect the peptides from exo-peptidase to maintain integrity of the peptide or protein for stability of cell adhesion and differentiation induction during the cell culture incubation.

Example 13

Selection of Peptides Based on Osteogenic and Functional Efficacy

Assays to determine the osteogenic activity of each additional peptide and combinations of peptides are performed as described herein for SEQ ID NO: 6. Osteogenic activity of each additional peptide and combinations of peptides are evaluated in cells, including quantifying amount of cellular AP activity, replication and differentiation induced in pre-osteoblastic cells. A total of 8000 data points are obtained for each cell replication and AP activity assay.

The biotinylated peptides are bound to the wells of streptavidin-coated plates. Coating concentration, temperature, time and washing condition are determined and optimized to give 25%, 50% and 100% (i.e., signal plateau) saturation of assay wells. Each additional peptide is tested in quadruplicate (n=4). The plates are stored at 4° C. until use.

The cell culture and osteogenic activity assays for single peptide activity are performed. Pre-osteoblastic hFOB1.19 cells are diluted in DMEM F12 50/50 medium supplemented with 10% FBS and 6418 antibiotic (Invitrogen). An aliquot (50 μL) of each dilution of cells is inoculated into the wells containing biotinylated peptide treated streptavidin-coated plates. Cells are cultured at 35° C. in a controlled atmosphere containing 5% $CO_2$ and 95% air. Half the volume of the culture supernatant is discarded daily and replaced with fresh medium to maintain amounts of cell produced autocrine factors in the medium and to introduce fresh nutrients to the cells.

Cell replication is measured (Cell Titer Glo luminescent assay; Promega) every 24 hours and significant differences are observed. Luminescence values for the peptides plateau and indicate maximum replication potential, and AP activity are measured.

Data show that the peptides induce significantly greater AP activity compared to controls. The level of osteocalcin, a biomarker for the bone formation process, in culture supernatant is measured at 48 hour intervals by ELISA. Osteogenic activity of each peptide is determined and analyzed including calculating amounts of AP and osteocalcin. Data show that the peptides increase the osteogenic differentiation potency of the cells. The osteogenic potency of cells contacted with peptides is greater than that of cells treated with controls such as tripeptide RGD and PepGen P-15.

Fibronectin-derived and collagen-derived cell adhesion peptides isolated previously are not specific for osteoblasts. In contrast, the peptides selected by the methods herein were specifically screened for activity for osteoblasts. Therefore, these selected peptides are more potent osteogenic peptides than other agents previously identified using other methods and systems, and are likely to be more specific in vivo and have fewer side effects.

A plurality of peptides in combination are added to osteoblasts cultured under a variety of conditions such as following osteoclastic bone resorption. Individual peptides and combinations of peptides have osteogenic activity and promote induction of osteoblast differentiation. Thus, data show synergistic osteogenic stimulation from combinations of peptides.

Example 14

Optimization of Peptide-Scaffold Compositions

Peptides are combined with scaffold materials, such that the resulting peptide-scaffold compositions induce osteogenic activity and osteoinductive activity.

Methods for binding a peptide to an apatite scaffold include extending pyrophosphate or polyphosphate (e.g., n is 3, 4, 5, 6, 7 or 8) on each N-terminus, immersing and immobilizing the peptides onto apatite, and observing multiple ionic interactions; forming calcium phosphate apatite compositions from polyphosphate and using the peptide as a nucleation core; and cross linking using ultraviolet light the peptides to the carbonate-containing apatite and observing covalent bonding between the peptide C-terminus ($COO^-$) and N-terminus ($NH_3^+$). The optimization of the peptide-apatite scaffold further includes producing a plurality of compositions that are characterized by varying: concentrations of peptides and apatite in the composition, binding conditions (e.g., pH 2-10, and 2° C.-37° C.), incubation times, porosities of the apatite, and presence of organic or inorganic agents.

Further, osteogenic peptides in Examples herein are synthesized and attached to other scaffold materials, including natural cancellous bone, demineralized natural cancellous bone, collagen, calcium phosphate, or hydroxyapatite. Each of these scaffold materials are optimized by evaluating in vitro osteogenic results for multiple compositions that are characterized by having varying concentrations of peptides and scaffold, and incubation times.

The peptide-scaffolds are evaluated under stringent experimental conditions in vitro as shown in Examples herein. The quantification includes quantifying cellular ATP and AP activity. The data show that that optimized peptide-scaffold compositions, including single peptides and combinations of peptides, increase the osteogenic differentiation potency of the cells, for example hMSC cells, compared to results for controls.

Example 15

In Vivo Evaluation of Peptide-Scaffolds Using an Ectopic Bone Formation Model

The osteoinductive activity of peptide-scaffold compositions is evaluated using an in vivo ectopic bone formation model in male rats. National Institute of Health (NIH) guidelines for the care and use of laboratory animals are followed (NIH publication #85-23 Rev. 1985).

Animals are divided into multiple treatment groups, with multiple animals per group, and are anaesthetized with intraperitoneal administration of sodium pentobarbital (5.0 mg per 100 g of body weight).

The implantation area is disinfected and animal are implanted in each of the left calf muscles and right calf muscles with each of the peptide-scaffold compositions. At least one animal is implanted with a control, and a scaffold having no bound peptide. The peptide-scaffold compositions implanted into the implantation sites (i.e., left and right calf muscles) have different concentrations of the peptide: a low peptide concentration, and a high peptide concentration.

The animals are sacrificed and implants and surrounding tissue are harvested and placed in ice-cold 15 mM sodium chloride (NaCl), 3 mM sodium bicarbonate ($NaHCO_3$) buffer. Each implant is then weighed and bisected. One-half of each specimen is placed in 5% formaldehyde solution buffered with 100 mM cacodylate. The remaining one-half amount of the specimen is re-weighed, placed in two milliliters of freshly chilled formaldehyde and cacodylate buffer and homogenized.

The specimen samples are spun in a centrifuge at 2500 g and are assayed by atomic absorption spectrophotometry for amount of acid-soluble calcium (e.g., milligrams of calcium per gram weight of wet tissue). Supernatants are assayed for amount and activity of AP, acid phosphatase, tartarate resistant acid phosphatase (10 mM sodium tartarate), and soluble protein. The assay values are expressed as units of enzyme activity per milligram protein.

The formaldehyde-fixed implants are dehydrated by ethanol washes and are embedded in methyl methacrylate. Each implant is cut into multiple levels (e.g., two, three, four etc) and sections that are 400 pm apart. Sections were stained including using toluidine blue for analysis of cartilage matrix metachromasia, von Kossa's stain for mineral deposition analysis, and hematoxylin and eosin for evaluation of the implant border and cellular detail. The sections are placed on a Zeiss Axiophot Microscope and analyzed with a Quantimet 520 Image Analysis System (Cambridge Instruments, Cambridge, UK) interfaced with a microscope using a chalnicon type video camera (Hamamatsu Photonics; Bridgewater, N.J.).

Sections are evaluated histometrically at multiple magnifications (e.g., 12.5×, 25×, and 40×). Quantification is determined by densitometric recognition of gray levels controlled through an analog-digital converter and algorithmic conversion of pixel point number to area measurements. Each implant's total surface area value is identified by manual outlining the video images of hematoxylin and eosin-stained sections. Mineralized tissue area covered by the von Kossa's stain is detected by a digital image analysis Quantimet computer (Cambridge Instruments Inc., Cambridge, England). The histometric values are expressed as the mean of the fractional ratio of mineralized area to total implant surface area. The biochemical and histometric values are then analyzed for statistical significance, for example by analyzing the data using Student's t tests and Fisher's protected least significance difference test. The level of significance for the implants tested is $p<0.05$.

The peptide-scaffold compositions are observed to produce and stimulate greater osteoinductive activity in the model than the controls. The peptide-scaffold compositions shown herein are also evaluated using an in vivo model.

Example 16

In Vivo Evaluation of Peptide-Scaffolds in a Cranial Defect Model

The osteoinductive and osteogenic activities of the peptide-scaffolds compositions is determined using a critical cranial defect model in vivo.

Sprague-Dawley rats (male, 8 weeks old) that have critical cranial defects are divided into two sets of four treatment groups, with six animals per group. The animals are anaesthetized. Each of the cranial defects (8×8 mm) is implanted with a scaffold only, a control, or one of the peptide-scaffold compositions.

One set of animals is sacrificed four weeks after implantation of the compositions, another set is sacrificed eight weeks after implantation of the compositions. Tissue samples are assessed for bone growth using multiple techniques including contact radiography, histology, histopathology, and micro computed tomography (μCT).

The cranial tissues of the animals are harvested and fixed for two days in 10% neutral buffered formalin (NBF). After fixation, the tissues are decalcified for two days with 10% formic acid. Radiological examinations (X-rays) are performed to determine the amount of decalcification and if additional decalcification is needed. After decalcification, the samples are dehydrated using alcohol, cleared in xylene, and are embedded in paraffin.

Samples are made into sections using a rotary microtome. The sections include the coronal plane through the widest area of the cranial defect. Nuclei present in the sections are stained with toluidine blue. The sections are analyzed histologically and histopathologically using the scoring scale shown in Table 2.

The peptide-scaffold compositions are observed to be histologically and histopathologically stable, and also stimulate greater osteoinductivity and are osteogenic potency in vivo than any of the commercially available peptides and compositions.

TABLE 2

Histologic scoring scale for the animal cranial tissues

| Characteristic analyzed | Grading | Score |
|---|---|---|
| amount of area cover by osseous tissues | >75% | 4 |
| | 50-75% | 3 |
| | 25%-50% | 2 |
| | 5-25% | 1 |
| | <5% | 0 |
| new bone thickness | >twice normal | 4 |
| | twice normal | 3 |
| | normal | 2 |
| | half normal | 1 |
| | none | 0 |
| defect bridged by new bone formation | complete | 4 |
| | moderate gaps | 3 |
| | small to moderate gaps | 2 |
| | little stumps | 1 |
| | none | 0 |
| matrix carrier remnant | >75% | 4 |
| | 50-75% | 3 |
| | 25%-50% | 2 |
| | 5-25% | 1 |
| | <5% | 0 |

TABLE 2-continued

Histologic scoring scale for the animal cranial tissues

| Characteristic analyzed | Grading | Score |
|---|---|---|
| Inflammation | severe | 4 |
| | moderate to severe | 3 |
| | moderate | 2 |
| | mild | 1 |
| | none | 0 |
| Fibrosis | severe, many whirling bundles | 4 |
| | moderate to severe, some whirling bundles | 3 |
| | moderate, densely arranged | 2 |
| | mild, loosely arranged | 1 |
| | none | 0 |

What is claimed is:

1. A peptide composition comprising a peptide having the amino acid sequence selected from the group consisting of SEQ ID NOs: 2-12, wherein the amino acid sequence has affinity for an extracellular matrix (ECM) component.

2. The peptide composition according to claim 1, wherein the ECM component is selected from the group consisting of an aggrecan, a collagen, and a hyaluronan.

3. The peptide composition according to claim 1, wherein the amino acid sequence comprises a cell stimulatory activity for at least one of growth and differentiation.

4. The peptide composition according to claim 3, wherein the activity stimulates at least one of a pre-osteoblastic cell and an osteoblast cell.

5. The peptide composition according to claim 3, further comprising affinity for an extracellular matrix (ECM) component.

6. The peptide composition according to claim 3, wherein the stimulatory activity is greater than a control comprising at least one of RGD tripeptide and GTPGPQGIAGQRGVV (SEQ ID NO: 24).

7. The peptide composition according to claim 1, comprising at least about 11 amino acids to about 100 amino acids in length.

8. The peptide composition according to claim 1, comprising at least about 20 amino acids to about 50 amino acids in length.

9. The peptide composition according to claim 1, wherein the amino acid sequence comprises an amino acid analog, an amino acid derivative, or a conservative substitution of an amino acid residue.

10. The peptide composition according to claim 9, wherein the amino acid analog-containing peptide is resistant to protease and peptidase degradation in presence of serum, compared to a control peptide identical in sequence and lacking the amino acid analog.

11. A peptide bone-substitute scaffold complex comprising: a bone-substitute scaffold selected from at least one of: natural cancellous bone, demineralized natural cancellous bone, collagen, calcium phosphate, and hydroxyapatite; and a peptide having the amino acid sequence selected from the group consisting of SEQ ID NOs: 2-12, wherein the amino acid sequence has an affinity for an extracellular matrix (ECM) component.

12. The complex according to claim 11, wherein the peptide and the bone-substitute scaffold are non-covalently bound.

13. The complex according to claim 11, wherein tile peptide and the bone-substitute scaffold are covalently bound.

14. The complex according to claim 11, wherein the peptide is linear.

* * * * *